(12) United States Patent
Rappaport

(10) Patent No.: US 7,739,123 B1
(45) Date of Patent: Jun. 15, 2010

(54) METHOD, APPARATUS AND SYSTEM FOR PROVIDING HEALTH INFORMATION

(75) Inventor: Alain T. Rappaport, San Mateo, CA (US)

(73) Assignee: Microsoft Corporation, Redmond, WA (US)

( * ) Notice: Subject to any disclaimer, the term of this patent is extended or adjusted under 35 U.S.C. 154(b) by 2005 days.

(21) Appl. No.: 09/591,769

(22) Filed: Jun. 12, 2000

Related U.S. Application Data

(60) Provisional application No. 60/140,102, filed on Jun. 18, 1999.

(51) Int. Cl.
G06Q 50/00 (2006.01)
G06F 7/00 (2006.01)
G06F 17/00 (2006.01)

(52) U.S. Cl. .................. 705/2; 707/2; 707/3; 707/102
(58) Field of Classification Search .................. 705/2, 705/3; 707/104.1
See application file for complete search history.

(56) References Cited

U.S. PATENT DOCUMENTS

| 5,583,758 | A | | 12/1996 | McDroy et al. |
| 5,768,578 | A | * | 6/1998 | Kirk et al. ............... 707/100 |
| 5,862,223 | A | | 1/1999 | Walker et al. |
| 5,862,325 | A | | 1/1999 | Reed et al. |
| 5,875,446 | A | | 2/1999 | Brown et al. |
| 5,924,074 | A | * | 7/1999 | Evans .......................... 705/3 |
| 5,953,704 | A | | 9/1999 | McDroy et al. |
| 5,970,499 | A | | 10/1999 | Smith et al. |
| 5,978,799 | A | | 11/1999 | Hirsch |
| 6,067,552 | A | | 5/2000 | Yu |
| 6,073,106 | A | * | 6/2000 | Rozen et al. .................. 705/3 |
| 6,263,330 | B1 | * | 7/2001 | Bessette ....................... 707/4 |
| 6,266,675 | B1 | * | 7/2001 | Evans et al. ............. 707/104.1 |
| 6,370,527 | B1 | * | 4/2002 | Singhal ........................ 707/6 |
| 6,438,533 | B1 | * | 8/2002 | Spackman et al. ........... 706/45 |

FOREIGN PATENT DOCUMENTS

JP      06290244 A   * 10/1994

OTHER PUBLICATIONS

Dyanchenko I.M.; Derkovskii M.M.; Rostkovskii V.S.; et al. "Mathematical software for automatic acquisition and storage of medical information." Dec. 1, 1973, Biomedical Engineering, vol. 7, No. 1, pp. 22-26.*

* cited by examiner

*Primary Examiner*—Robert W Morgan
*Assistant Examiner*—Rachel L Porter
(74) *Attorney, Agent, or Firm*—Turocy & Watson, LLP

(57) ABSTRACT

According to one aspect of the present invention, a method is provided in which information about a patient is received. The information about the patient may include diagnosis information based upon a diagnosis of the patient performed by a healthcare provider. Upon receiving the information about the patient, a query function is performed to retrieve from a database a list of data sources that correspond to the information received. One or more documents are generated that contain the list of data sources retrieved from the database.

24 Claims, 19 Drawing Sheets

FIG. 15a

WEB PAGE personal health care info site
medstory.com

Date: January 12, 1999 - Physician: A.C. Epton, MD; 555-343-5555
Julian Smith: Scarlet Fever  Age: 6 - MyMedStory™ #012654-72

- HEALTH PLAN SERVICES
- IPA Services
- HEALTH PLAN INFO

■ MyMedStory:

→ Prescription: AMOXICILLIN (a-mox-I-SILL-in) + Clavulanate
  o Brand Name: AUGMENTIN®
  o 1 1/2 (one and a half) teaspoon twice a day for 10 days
  o Make sure you remember to "shake it and give it"

→ IMPORTANT:
  o Do not stop the treatment before the full 10 days, even if all symptoms have disappeared. This is VERY IMPORTANT, as other and serious problems (complications) may otherwise develop.
  o In case of an additional or increased rash, hives, breathing difficulties, dizziness, zero-search™

SCARLET FEVER

- ZeroSearch Site 1
- ZeroSearch Site 2
- ZeroSearch Site 3
- ZeroSearch Site 4

FIG. 15b

WEB PAGE

○ In case of an additional or increased rash, hives, breathing difficulties, dizziness, swelling of the lips, tongue, face or eyes, or any other rapidly evolving difficulty, do contact your doctor IMMEDIATELY!

→ contact your drugstore if needed:

 Drugstore

→ INFORMATION:

○ Julian actually has a "Group A Beta Hemolytic Streptococci" infection, or "Strep Throat", a common infection in children. Because he has also a typical rash as well, he has in fact a form of "Scarlet Fever". For detailed information from selected sources of medical information, go to zero-search.™

 ZeroSearch Site 4

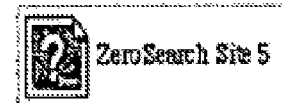 ZeroSearch Site 5

 ZeroSearch Site 6

AUGMENTIN®

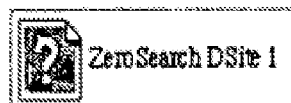 ZeroSearch DSite 1

■ MANAGING JULIAN'S TREATMENT

→ YOU ARE NOW ON DAY TWO!

FIG. 16

METHOD, APPARATUS AND SYSTEM FOR PROVIDING HEALTH INFORMATION

RELATED APPLICATIONS

This application claims the benefit of U.S. Provisional Application No. 60/140,102, filed Jun. 18, 1999.

FIELD OF THE INVENTION

The present invention relates generally to the field of information processing. More specifically, the present invention relates to a method, apparatus, system, and machine-readable medium for providing targeted health information to patients following their visits to their healthcare providers, based upon information about the patients provided by one or more sources including their healthcare providers.

BACKGROUND

Getting relevant and useful health information has been a great concern for many people. Nearly half of the adults spending time on-line have visited health-related sites. Furthermore, some of the most desired types of on-line health information are "information from my doctors' office" or from "national medical experts". This comes as no surprise since according to a most recent analysis of the health care system in a prestigious US medical journal, "in one survey, half of the patients reported having left their physician's office not knowing what they had been told or what they were supposed to do".

However, health or medical information is notoriously complex and difficult to evaluate for non-MD individuals. Finding the proper and precisely relevant information in the myriad of medical web sites is a difficult and time-intensive process. Often, it simply cannot be successfully achieved since the patient does not understand well enough the condition, and thus even less so how to formulate queries for searching in various search engines and web sites.

There are more than 10,000 medical or health-related web sites on the web at the present time, and health care is a rapidly growing Internet content area. These web sites can be generally classified or categorized as follows based upon the types of information that they provide:

Medical Information Content Providers: these sites are broad scope or specialized repositories of medical information.

Pharmaceutical Information Content Providers: these sites are similar to the above but focused on drug information.

E-commerce: on-line drugstores are predominant in this category, adding their operations to the traditional physician/prescription/drugstore relation. This category also includes companies that sell medical equipment or health insurance policies.

Health Management Companies: these companies provide tools to help customers manage complex or chronic diseases such as diabetes or other health conditions.

Health-Benefit Information: this category entails essentially information sites from managed care organizations, providing a mix of news and access to benefits descriptions and billings for members.

Health Care Business Infrastructure: these companies provide Internet-based software solutions to increase the internal productivity of health care organizations.

The combination of these offerings and services makes it clear that the health care industry is on the verge of an information-based revolution that will have profound consequences. However, medicine is not trivial and "one thing to keep in mind when you're researching information online is that your computer doesn't have an M.D." [C|net, 1999]. It has already become critical to enhance and yet simplify the health care consumer's experience with new and innovative services that are targeted, personalized and that can become an integral part of health care delivery.

Patients or health care consumers thrive to become more informed and empowered with relevant information. One of the types of information they desire the most is "information from my own doctor's office" [*JAMA*, Editorial, Digital Doctoring, Oct. 21, 1998], as well as information from national medical experts [*Cyber Dialogue/FIND/SVP*, 1998]. Indeed, the health care system, under considerable economic pressures that are unlikely to disappear anytime soon, has transformed the physician-patient relationship.

In general, interactions with physicians are shorter. Diagnoses are often sent directly to the managed care organization and the patient receives no clear information about his or her condition, problem, or other aspects of his or her heath. Also, the prescription can be sent directly to the drugstore, on-line or not. This often leaves the patient with barely any notion of what the diagnosis is and how to deal with it, including finding further information about it. "In one study, half of the patients reported having left their physician's office not knowing what they had been told or what they were supposed to do." [The American Health Care System, T. Bodenheimer, *New England Journal of Medicine*, Feb. 18, 1999]. Educating the patient is a critical need. Not only "well-informed patients are often healthier patients" [*Medical Economics*, Why You Should Welcome the New Assertive Patient, September 1997], but "the use of Internet-based health information leads to better health care" [*Managed Health Care*, G. Moore].

Pediatrics and Women's' Health, for example, are two major topics on which medical information is sought on-line. "In 1998, 27% of adults with children said they go online in search of children's health content, up from 15% of parents the previous year" [*Cyber Dialogue, Inc.*, The Health Care Industry in Transition, 1998]. In the same year, women constituted 46% of all adults on-line and Women's Health has been a major topic online for 31% of all online users.

However, in spite of the great number of health-related web sites available on the Internet, it is still very difficult to obtain relevant, useful and personalized health information on the Internet for various reasons, some of which are mentioned below:

There is a very large number of sites from which to retrieve information. The patients or healthcare consumers often do not know which sites would be good or relevant for their informational purposes.

The sites are not targeted enough. "The biggest obstacle you're likely to face online is information overload." [*Fortune*, Where to Find Medical Advice on the Web, Mar. 17, 1997]. There is indeed too much information, most often poorly organized or presented. The patients or consumers are required to perform complicated searches and then need to refine searches and use filters in order to reach the desired information, if any. These search mechanisms also often require the users to use the correct terminology for searching as well the minimal skills to formulate more complex queries. The patients or healthcare consumers often do not have the time to search for information. They also do not have the time to filter or eliminate irrelevant or extraneous information from a vast amount of information available on the Web.

Sites are very uneven in quality or in organization, making them more difficult to use. Typical search interfaces may be difficult to use and presentation of search results may not be well organized to enable the average users to select relevant information for their purposes.

In short, browsing the web for medical or health-related information is actually far from being a simple task. It requires a significant amount of time and familiarity with various jargons, terminology, synonyms and other idiosyncrasies and complex issues of the health care field. For most health care consumers, it is an out-of-context and laborious process.

Accordingly, there exists a need for the health care consumers to efficiently and effectively locate and obtain relevant, useful and personalized health-related or medical information without laborious and intensive searching through various web sites on the Internet.

SUMMARY OF THE INVENTION

According to one aspect of the present invention, a method is provided in which information about a patient is received. The information about the patient may include diagnosis information based upon a diagnosis of the patient performed by a healthcare provider. Upon receiving the information about the patient, a query function is performed to retrieve from a database a list of data sources that correspond to the information received. One or more documents are generated that contain the list of data sources retrieved from the database.

BRIEF DESCRIPTIONS OF THE DRAWINGS

The features and advantages of the present invention will be more fully understood by reference to the accompanying drawings, in which.

Figure 15C:
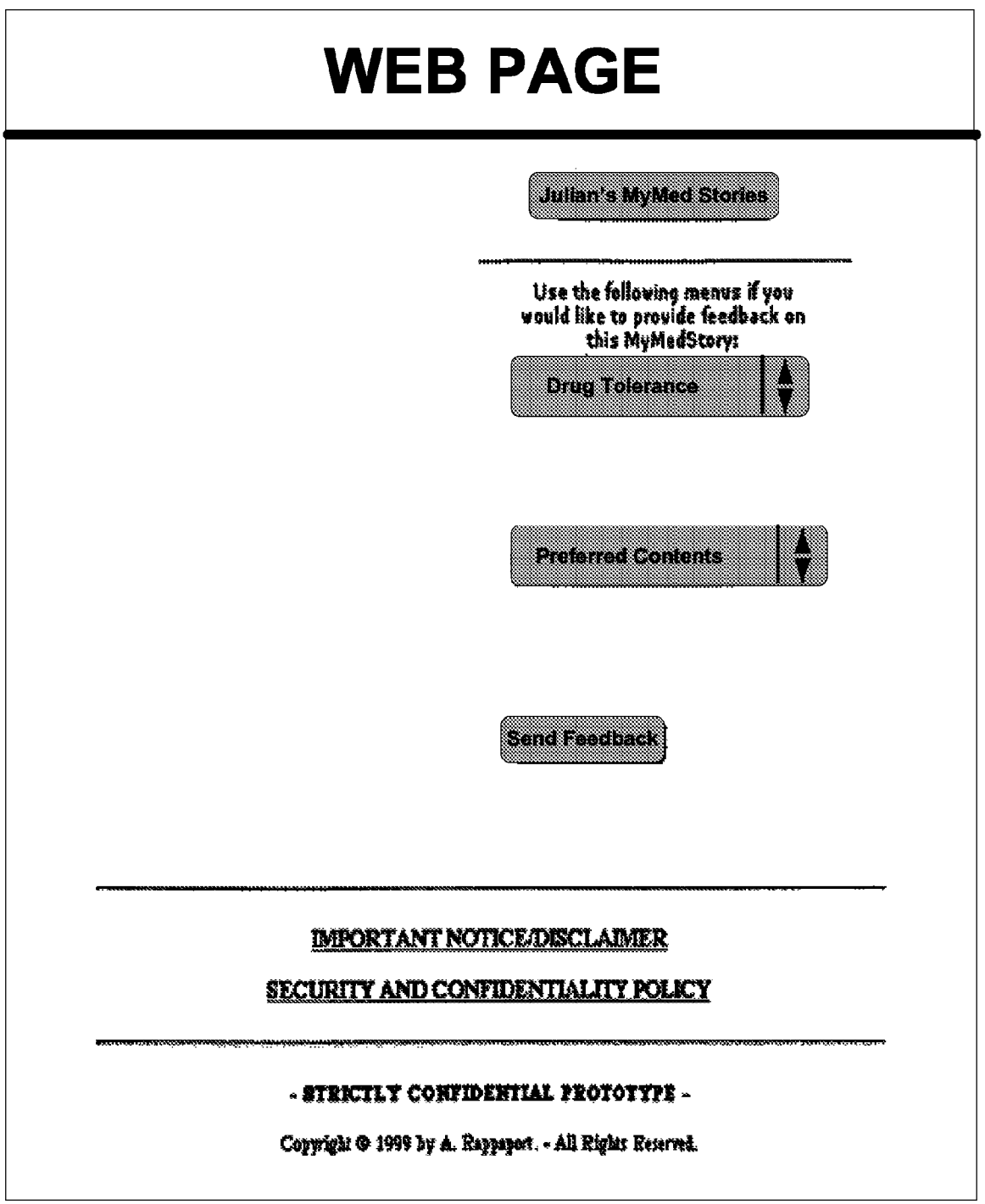
Figure 16:
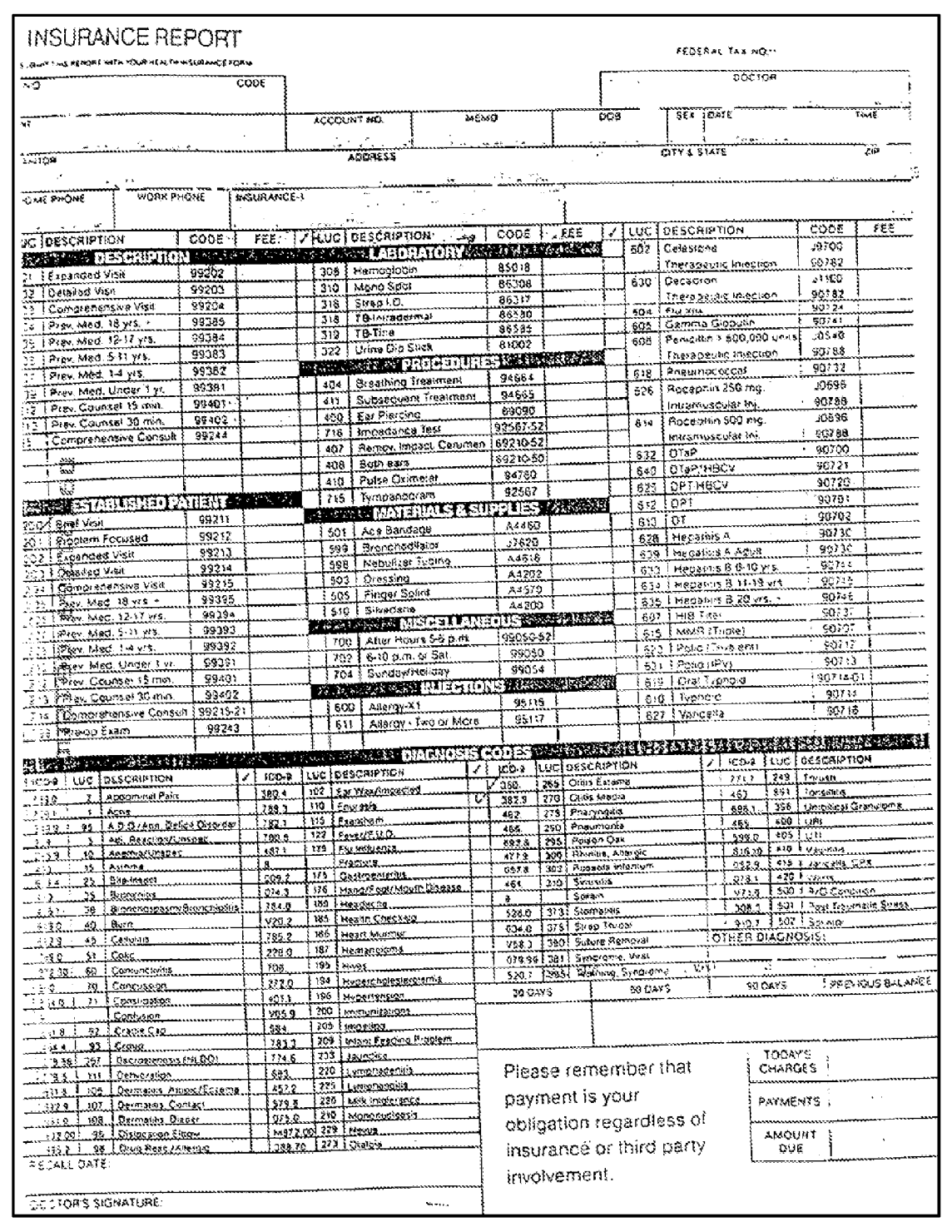

FIGS. 15A, 15B, and 15C illustrate an example of one embodiment of a web user interface for presenting personalized health-related information and links to other sources of relevant information, in accordance with the teachings of the present invention; and FIG. 16 shows an example of an insurance report containing codes according to the International Classification of Disease (ICD).

DETAILED DESCRIPTION

In the following detailed description numerous specific details are set forth in order to provide a thorough understanding of the present invention. However, it will be appreciated by one skilled in the art that the present invention may be understood and practiced without these specific details.

In the discussion below, the teachings of the present invention are utilized to implement a method, apparatus, system, and machine-readable medium to provide targeted and personalized health-related information to healthcare consumers including patients. In one embodiment, information about the patient is received from one or more sources including the patient's healthcare provider or physician. The information about the patient received from the various sources may include clinical information and patient care information. The information about the patient may include patient identification data such as name, date of birth, gender, etc. and patient care delivery event information such as codes, prescription information, test information, etc. The information about the patient may include diagnosis information based upon a diagnosis of the patient performed by the healthcare provider. When the information about the patient is available, a query function is performed to retrieve from a database (also referred to as the ZeroSearch Database) a list of data sources (also called list of content links) corresponding to the information received. The information and data contained in the ZeroSearch database may include a "context-rich" directory of medical, clinical, and personal health management information and data. In one embodiment, one or more documents (also referred to as MyMedstory herein) are generated that contain the list of data sources retrieved from the ZeroSearch database. In one embodiment, the diagnosis information received may include one or more diagnosis codes indicating one or more conditions of the patient based upon the diagnosis performed by the healthcare provider. The one or more diagnosis codes, in one embodiment, are codes that are used according to the International Classification of Disease (ICD). The diagnosis information received may include one or more descriptions describing the patient's conditions and/or problems based upon the diagnosis performed by the healthcare provider. In one embodiment, the information about the patient may also include the patient's personal and profile information, prescription information, laboratory information, procedures information, materials and supplies information, and injection information, etc. that may or may not have corresponding codes. In one embodiment, upon receiving the information about the patient, a set of queries is generated containing query criteria based upon the information received. The set of queries is executed to retrieve from the database the list of data sources corresponding to the query criteria. In one embodiment, a data source is referenced by an address corresponding to a location where the respective data sources resides. The address corresponding to the location where the data source resides may be referenced by a Uniform Resource Locator (URL). In one embodiment, the one or more documents generated may be accessible by the patient via a computer network, for example via the Internet. In one embodiment, the patient is allowed to provide feedback or comments with respect to the information contained in the one or more documents. In one embodiment, the database is structured to include a list of codes where each code is used to indicate a condition and/or problem relating to the patient's health. For each code in the list, the database may also contain a list of one or more definitions of the respective code. In one embodiment, the database is used to store a list of data sources identified using the one or more definitions associated with each code. In one embodiment, the database is also configured to store a set of queries associated with each code. The set of queries associated with each code is constructed based upon the one or more definitions corresponding to the respective code. In one embodiment, the list of data sources associated with a particular code is obtained by running the corresponding set of queries against various databases available on the World Wide Web (WWW) to identify one or more documents or content links that match the query criteria specified in the corresponding queries. In one embodiment, a selection process is performed to select the list of data sources for the respective code from the documents or content links identified from the various web databases. The teachings of the present invention are applicable to any search engines and directory systems that are used to provide health-related information to users. The teachings of the present invention are also applicable to any method, system, or mechanism for providing health-related information to the users based upon query criteria submitted by the users or other sources. However, the present invention is not limited to providing health-related information to the users and can be applied to other types of information processing in other business areas or disciplines.

According to one aspect of the present invention, the system and method described herein are designed to provide information services to healthcare consumers by providing the patients or healthcare consumers with relevant and personalized health-related information that are tailored based upon their needs following their interaction with their healthcare providers. The relevant, personalized, and targeted health information is generated by the system and included in a document referred to as a "MyMedstory". Each MyMedstory may have a unique identifier. In one embodiment, each MyMedstory is designed to contain basic patient and provider information, health plan information and services, Zero Search™ and other information services relevant to each specific health consumer.

Access to a MyMedstory "document" by a patient can be achieved in various ways. In the following description, the Internet/World-Wide-Web model is used for explanation and illustration purposes. Accordingly, a MyMedstory can be a "web document" or "web site" accessed by the Patient via the Internet. However, other communications means may be used, such as television, cable, information appliances, telephone, handheld devices and other technologies. The Zero-Search Database is independent of the media or user interface. In the television example, the service delivered to the patient may be a series of videos or programs directly relevant to the current condition, as well as all other information components.

Communications between the different entities (e.g., Provider, Health Plan and Health Care Organization, Provider Organization and Medstory system, other organizations or companies that may be provide information) can take place in any manner (including but not limited to telephone, fax, Internet, email, world-wide-web, wireless networks). Providers, for example, could provide code and other information to Medstory using worldwide web clients, wireless clients, telephone, and others.

Communications and interoperability between the different software and hardware components can make use of different systems including, but not limited to, CORBA, DCOM, COM, RMI or other RPC. Protocols can also vary, including, but not limited to, HTTP, SMTP, NNTP or "push" protocols. Different solutions can be implemented concerning the security, privacy and confidentiality of information, including for example, secure http ("https") for security.

Contents may be implemented in any language (or mix of languages) including, but not limited to HTML (HyperText Markup Language), XML (Extensible Markup Language), SGML (Standard Generalized Markup Language), Java, C, C++, and others. Programmatic interfaces for modifying content can be implemented following different specifications, including DOM (Document Object Model) as an example. Other delivery technologies such as television or handheld devices may require other languages or formats (e.g. Wireless Markup Language, WML, for handheld devices). Final rendering could also be provided in Braille, speech generation systems or other interfaces.

According to the teachings of the present invention, the system and method described herein are designed to provide an innovative and powerful set of Internet-based services to eliminate the complexity of obtaining and using on-line health information and to provide rapid, highly targeted, direct-to-customer (DTC) services, following each interaction between patients and health care providers.

In one embodiment, upon receiving information about a patient's visit to the provider, the system and method described herein are designed to generate a web document, called MyMedstory™, which can be considered the equivalent of a personal, confidential and secure portal into services directly and specifically relevant to the patient's current condition. In one embodiment, a MyMedstory may also be generated following visits that result in no prescription and a common diagnosis or even a problem.

The MyMedstory™ can be considered as a "meta-service", with direct, zero-search access to relevant and targeted information in selected medical information or service sites. The Medstory system is designed to function as a meta-information organizer, specializing in rapidly filtering, targeting and verifying the quality of relevant information on a wide variety of medical matters, and then providing the results to the customer.

In addition, the Medstory system can help "augment" the prescriptions, i.e. emphasize important details that are related to the condition. This type of information is not usually available to on-line drugstores that receive only the prescription information and may have a patient profile, but the usefulness of the latter may be limited (e.g. ampicillin should not be prescribed during a mononucleosis, but no pre-determined profile will help here; e.g. it is imperative to take the full ten days of antibiotics to treat strep throat, even if the symptoms have completely disappeared).

Furthermore, the provider (e.g., physician, dentist, etc.) can contribute comments that will be directly added to the MyMedstory, enhancing the patient/provider relationship. As mentioned above, it has been determined that the patients would prefer to receive additional information from their own doctors. The Medstory services therefore can be used to enhance the patient/doctor communications and increase the likelihood of better patient management and overall efficacy of the practice.

Medstory's services can be considered "real-time" in terms of health care delivery. Each diagnosis and/or prescription is to be followed by the construction of a personalized on-line MyMedstory available as soon as possible. Furthermore, based on the reception of other low-resolution medical information, Medstory can provide longitudinal (historical) health information services (e.g. growth curves for children; vaccination schedules; pregnancy-related information in normal or high-risk pregnancies; condition management tips; etc.), as well as the past "collection" of MyMedstories.

With the generation of MyMedstory documents which can be accessed by the patients from home via the Internet, the patients can perform, all within one document accessed securely with authentication:

Direct, zero-search access to quality web-based documents (text as well as video, audio, etc.) pertinent to the conditions/problems/issues in question, from trustworthy medical content databases.

Direct access to information on the prescription and course of treatment (e.g. what do to if symptoms disappear, or others appear) in the context of the specific clinical, surgical or other condition.

Direct access to laboratory data if applicable and their interpretation, with zero-search access to relevant web-based information.

Direct e-commerce access (e.g. to the patient's preferred on-line drug provider or to the optimal choice between alternatives; e.g. to purchase OTC products directly part of the treatment recommendation).

Direct, zero-search access to relevant e-group activities (chat rooms, support groups, etc.).

Direct access to personal historical health information through the history or collection of MyMedstories.

Direct access to benefits-related information concerning the current visit, procedures and other expenses, including pro-active information and intervention programs from the health care plan or organization concerned.

Direct on-line information mediation services (e.g. therapeutic management, health risk assessment, etc.)

In addition, Medstory's services are unique in their ability to use "low-resolution medical data" (e.g. diagnosis codes, procedure codes, gender, age, weight, height, etc.) to direct search to relevant documents on numerous medical web content sites and deliver as soon as possible a personal on-line document, the MyMedstory.

Pointers are not limited to information pages but also include selections of chat, support groups and other e-group related services, videos and other documents, when applicable.

By using various methods and mechanisms described herein according to the teachings of the present invention, a large network of physicians would be able to reach their patients through the MyMedstory, providing targeted information and different levels of services, from news to health management, preventive care and custom, personalized communications.

The MyMedstory content and related services can be viewed as a virtual extension of the patient's interaction with his healthcare provider (e.g., a doctor's visit), an achievement that can be done even without more information from the doctor's office than the mandatory diagnosis code for insurance payment. It renders seamless the process, otherwise ruptured, of health care continuity between the doctor's office and the patient's home, by providing the around-the-clock information services to help the patient obtain useful, relevant, and personalized information that is organized and targeted to meet the patient's personal needs.

It is important to note again that this lack of information has a profound impact on even the most common types of diseases. The "scarlet fever" mentioned as an example is a benign condition compared to a chronic disease or cancer. However, a child with a very high fever, a sand-paper rash, a severe sore-throat and other symptoms is not a happy sight for the parents. The parents are likely to call the doctor's office again, bring the child back for another visit or to check an unaffected sibling by fear that he/she is also ill, without the proper disease management information.

One of the additional benefits and features provided by the MyMedstory is that it creates, de facto, a light form of patient record by keeping a history (also referred to as a collection) of MyMedstories. Although the latter may not use the high-resolution information of a classic medical record, they do contain very useful historical information.

The MyMedstory can be considered a "life-wide" intervention program, where patient education can be achieved not only in complex situations but also for seemingly simple health care events. One of the economic results that can be achieved by the MyMedstory is likely to be a decreased number of doctor visits due to better information on conditions, treatment management and self-evaluation of outcomes. By knowing what the condition is, what to expect and how to manage even a common disease of a child, the likelihood of a subsequent visit to the physician can be reduced. Likewise, misuse of emergency services can also be avoided. At times, the number of visits may be increased because of the relevant and useful information provided in the MyMedstory. However, the benefit in these cases is that problems can be identified or detected earlier (e.g., in the case of pregnancy supervision or prenatal care).

Furthermore, educating the patient means providing reliable and high-quality information, one of the benefits and advantages provided by a focused and targeted MyMedstory. Too much information of uneven quality as found when navigating the net might actually increase the risk of returning and increasing costs in the end. The MyMedstory could help significantly in focusing and channeling the information for each individual patient following an interaction with his provider, thus lowering the risk of returning to the provider and better preparing the interaction with other providers or simply complying with the recommended advice.

The use of the Web, the content aggregation functions and the potential for a wide variety of communications with the patient makes the MyMedstory highly cost-effective, a unique positioning in the health delivery system. As noted earlier, the MyMedstory can also be used to implement other condition or therapy-specific intervention programs, thereby decreasing significantly the implementation costs of those plans.

Various sources may provide the Medstory system with the necessary information (e.g., diagnosis, other low resolution medical data or "LRMD", benefits, other services, etc.) for the generation of a MyMedstory for a patient, including:

Physicians: data entry at point-of-care and secure transmission to the system diagnosis or problem information, code as well as patient identification. The transmission could result in the issuance to the point-of-care an authentication key for the patient.

IPAs or other Provider Organizations: related services and information, sent to Medstory for inclusion in the MyMedstories or accessed through their own site directly referenced in the MyMedstory (zero-search).

Health Care Organizations (HCOs) or Health Plans: personal benefits information forwarded to Medstory over secure IP lines, or directly accessed through their own site referenced in the MyMedstory, and targeted intervention programs.

Clinical Laboratories: test related information.

Different types of information are likely to be received by Medstory at different times. In one embodiment, diagnosis information should arrive first with the detailed prescription (if any). Benefits information, however, will arrive later as it needs to be sent to the Health Plan or HCO first.

The physicians' offices are likely to be involved in the process, to transmit the correct diagnosis or problem information (e.g., ICD-9 codes), and the prescription information. It should be noted again that the ICD-9 code information should provide enough information for the generation of a personalized MyMedstory. In conjunction with a patient profile (including date of birth, siblings, other volunteered information) the personalization and targeting of the MyMedstory can be increased.

One of the aspects of the present invention is the mixed-initiative (machine+people) approach to "information synthesis". There is an initial investment to derive zero-search links for the main diagnoses in each segment. However, selected zero-search links (also called information or data sources) for a given condition can be used for the generation of other MyMedstories with this diagnosis information, although there might be some additional refinement based on other medical data of a consumer-provided profile. The same is true for medications. Searches are performed periodically to stay current with the medical databases, detecting changes or revisions automatically.

Figure 1:
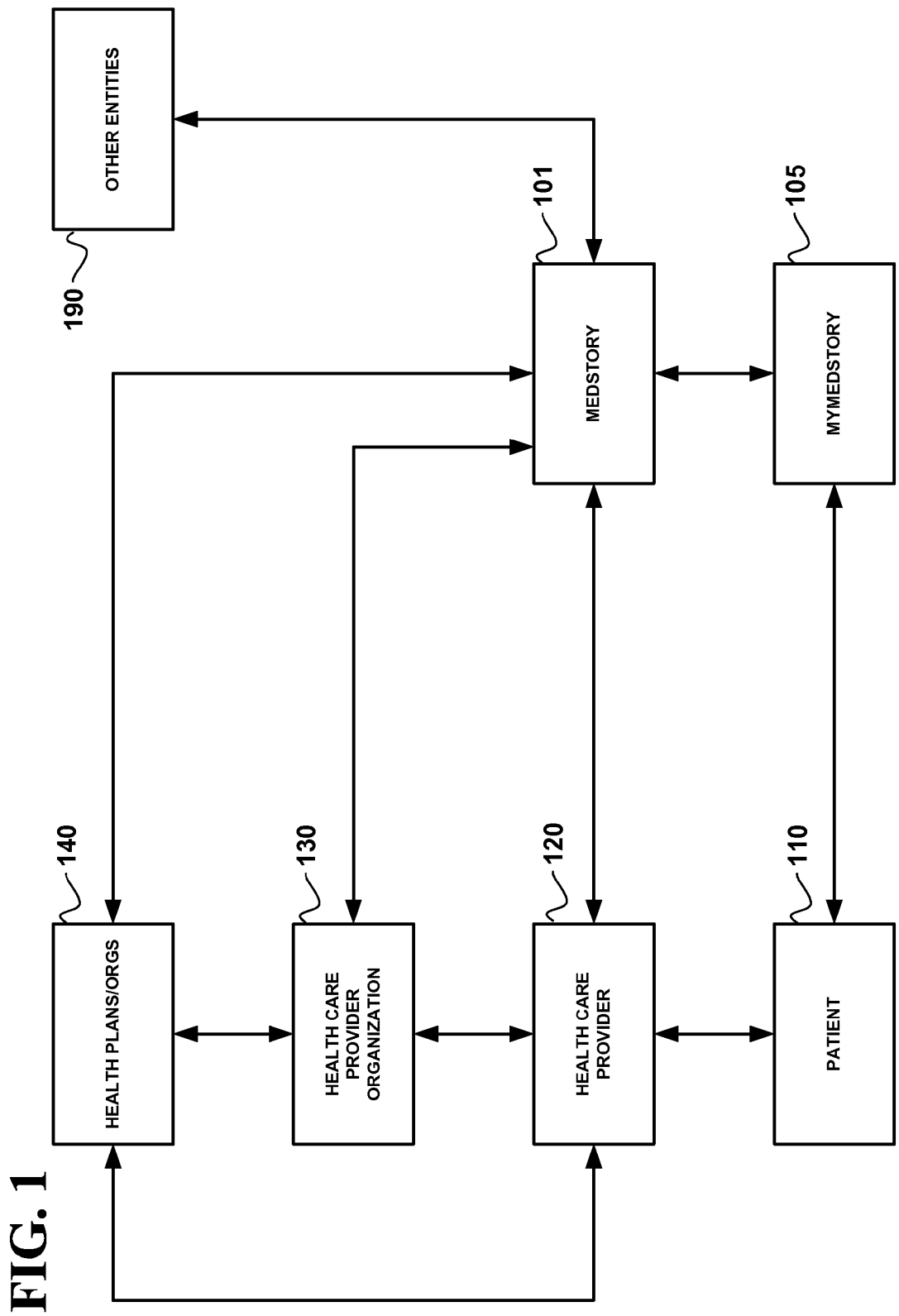
FIG. 1 illustrates a block diagram of one embodiment of a system according to the teachings of the present invention.

FIG. 1 illustrates a block diagram of one embodiment of a system environment and configuration 100 for providing targeted and personalized health-related information to patients following their interactions with their healthcare providers. In the present embodiment, various entities can be connected to a system 101 via a computer network. In one embodiment, the computer network can be a local area network (LAN), a wide area network (WAN), the Internet, or any combinations thereof. In one embodiment, the system 101 is an Internet-based system designed to perform various functions described in more details below. The various functions performed by system 101 include receiving information about the patient from various sources connected to the system 101 including the healthcare providers 120, the health care provider organizations 130, and the health plan organizations 140, and the patients 110, etc.; retrieving a list of data sources or content links from a database (also referred to as the Zero-Search database herein) corresponding to a set of queries generated based on the information about the patient received from the various sources; and generating one or more documents that contain the list of data sources retrieved from the ZeroSearch database, etc. that can be accessed by the patient via the computer network. The various functions performed by the system 101 also include building and maintaining the ZeroSearch database. The various functions performed by the system 101 are described in more details below.

Referring to FIG. 1, in one embodiment, the patients 110 can establish connections with the system 101 via the Internet. The patients 110 can access various documents (MyMedstories) that contain targeted and personalized health-related information that are generated by the system 101 upon receiving information about the patients following their interactions (e.g., visits) with their respective healthcare providers 120. The patients 110 can also provide to the system 101 their personal, profile information or other types of information that can be used by the system in generating the MyMedstory documents for the patients and maintaining the patient's medical/health history.

Continuing with the present discussion, in one embodiment, the healthcare providers 120 can establish connection with the system 101 via an Internet connection. The healthcare providers can transmit to the system 101 various types of information about the patient including the patient personal information, diagnosis information including diagnosis codes, low resolution medical information (e.g., weight, height, blood pressure, etc.), prescription information for prescription drugs and over-the-counter drugs, materials, supplies, or other physician-provided information or recommendations (e.g., counseling, education, diet, exercises, or other therapeutic services), and other comments. The healthcare providers 120 can also provide other types of information about the patient including vaccinations, procedures, preconditions, risks, etc. if applicable. The healthcare provider organizations 130 to which the healthcare provider 120 belongs may also have other relevant information including local health data and news, community health news, information relating to their own campaigns or programs concerning prevention, intervention, quality of care, cost reduction, etc.

Similarly, the health plan organizations 140 can establish connection with the system 101 via an Internet connection. The health plan organizations 140 can provide to the system 101 various types of information about the patient including the information available on the patient's record including but not limited to explanations of benefits, referral services, etc. The health plan organizations 140 can also provide information regarding the current conditions and other associated benefits as they are available. Other entities or players 190 can also be connected to the system 101 including laboratories, pharmaceutical companies, public health organizations, online drug stores, advertisers, etc. These various entities can also provide various types of information to the system 101 including targeted messages, general health-related information, specific health-related information, information concerning health-related issues and news, etc. The system 101, upon receiving the information about the patient from various entities connected to the system 101, performs various functions as described in more details below to generate one or more documents that contain targeted and personalized health-related information that can be accessed by the patients 110 via the computer network.

Figure 2:
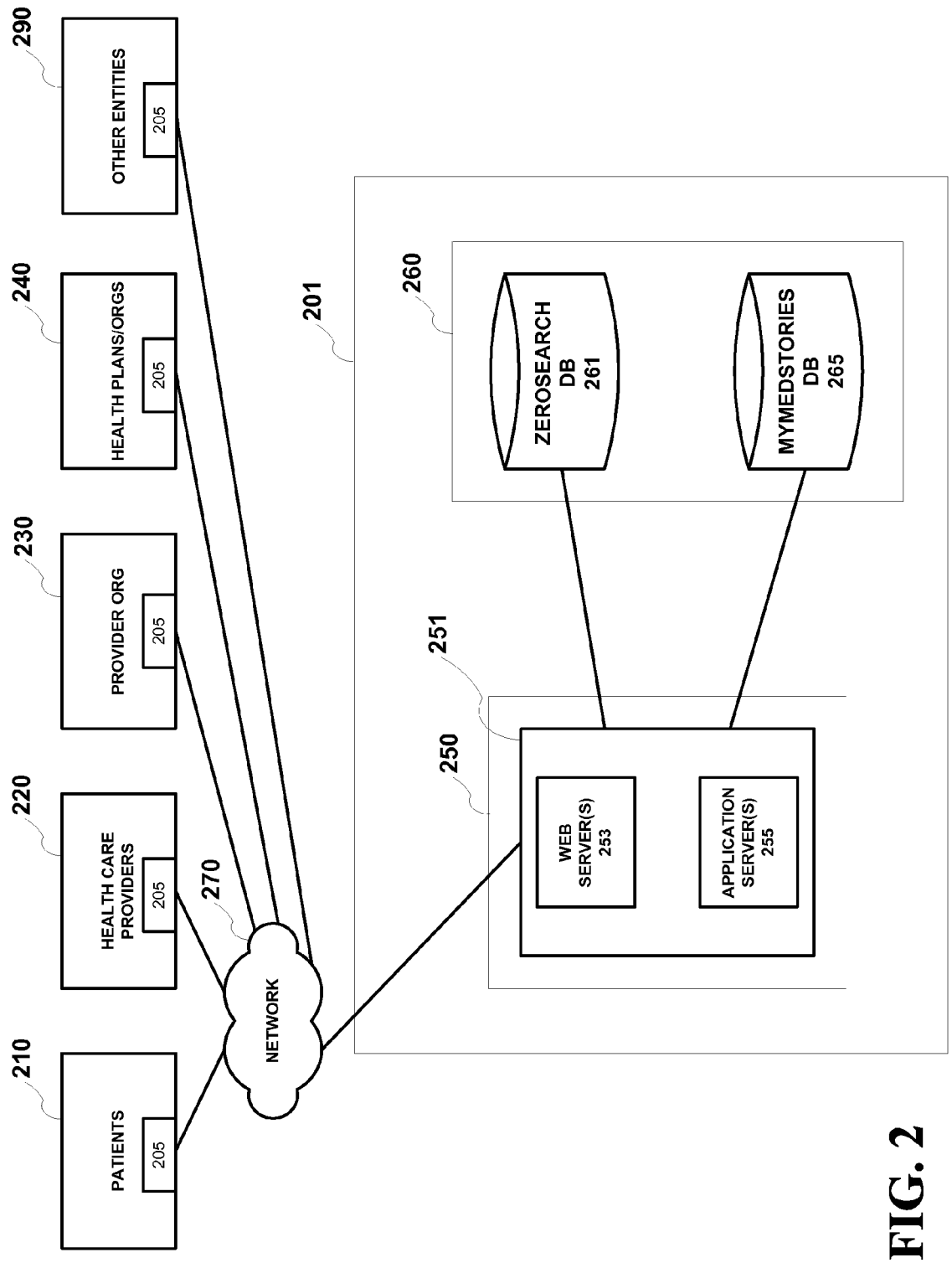
FIG. 2 shows a detailed block diagram of one embodiment of the system in FIG. 1.

FIG. 2 illustrates a more detailed block diagram of one embodiment of the system configuration 100 shown in FIG. 1. For clarity and simplicity, the discussion herein is focused on the interactions between the patients 210, the healthcare providers 220, and the system 201. However, everything discussed herein equally applies to other entities connected to the system 201 as well as in other environments. In one embodiment, the system 201 performs various functions based upon the information provided by the patients 210, the healthcare providers 220, the healthcare provider organizations 230, and the health plan organizations 240, etc. The various functions performed by the system 201 include generating the MyMedstory documents for the patients based upon the information received from the healthcare providers 220 and other sources, maintaining the ZeroSearch database that contains health-related information (e.g., content links), etc.

In one embodiment, the system 201 can be logically organized into two major subsystems or units: a server subsystem or unit 250 and a database subsystem or unit 260. The server subsystem 250, in one embodiment, contains one or more servers 251. The database subsystem or unit 260, in one embodiment, contains a database 261 (the ZeroSearch database) and a database 265 (the MyMedstories database). These various system components of the system 201 are described in greater detail below. Continuing with the present discussion, in one embodiment, the various entities can establish connection with the system 201 via the Internet and communicate with the system 201 using an Internet browser (also referred to as the client program). The various entities can establish connection with the system 201 using a router, a dial-up modem, or other methods of Internet connections available to them. The various entities can utilize an Internet browser to interface with the system 201 in order to provide information to the system 201 and access the various functions and features of the system 201. In one embodiment, the various entities connected to the system 201 can also use the browser client program to communicate with each other. In one embodiment, the system 201 can support both Microsoft® INTERNET EXPLORER® and Netscape® NAVIGATOR® browser software.

In particular, the healthcare providers 220 can use their browser client program to provide information about the patients 210 to the system 201. The patients 210 can use their browser client program to access the various MyMedstory documents generated by the system 201 following the interactions between the patients 210 and the healthcare providers 220. Other entities including advertisers 290, in one embodiment, can establish connection with the system 201 via the Internet using routers, dial-up modems or other methods of Internet connections available to them. In one embodiment, the advertisers 290 use an Internet browser to access the system 201 to place their advertisements into the system 201 that can be displayed to the various users of the system 201. For example, an advertisement submitted by one of the advertisers 290 can be selected by system 201 to display to the patients 210 when they access their MyMedstory documents.

Referring again to FIG. 2, in one embodiment, the server(s) 251 is connected to the clients 205 via the network 270. In one embodiment, the server 251 includes a web server 253 and an application server 255. The web server 251 is used to communicate with the client 205 (e.g., a web browser front end). In another embodiment, the web server 251 and the application server 255 can be merged. The application server 253, in one embodiment, includes one or more computer programs that are designed to perform various functions described herein. In one embodiment, the application server 253, in performing its various corresponding functions, accesses and stores data in various databases in the database subsystem 260, including the ZeroSearch database 261 and the MyMedstories database 265.

The ZeroSearch database 261, in one embodiment, is used to store health-related information that is used by the system 201 to generate the MyMedstory documents for the patients 220. The information stored in the ZeroSearch database 261 includes a list of diagnosis codes and other codes, one or more definitions for each code, a set of queries containing query criteria that correspond to the one or more definitions of each code, a list of contents links or data sources that are identified using the corresponding set of queries, etc. The structure and specification of the various types of information or data elements stored in the ZeroSearch database 261 are described in detail below. The ZeroSearch database 261 can be any type of storage medium including disk, tape, etc. In one embodiment, the ZeroSearch database 261 is configured as a relational database containing a set of various tables used to store various types of information associated with the various codes as described above. However, the teachings of the present invention are not limited to relational database structures and can equally apply to any other database or file structures including flat file structure, indexed file structure, hierarchical database structure, distributed database structure, object database, or any combinations thereof, etc.

In one embodiment, the MyMedstories database 265 is configured to store a list of patients and the MyMedstory documents generated for each patient in the list. Each MyMedstory document constructed can have a unique identifier. The MyMedstory documents stored in the database 265 can be accessed by the patients 220 via the application server 255. Accordingly, a patient can access not only a MyMedstory generated for him following the most recent visit to his healthcare provider but also previous MyMedstory documents generated for him for previous interactions or visits with the healthcare provider. As such, the collection of the personal MyMedstory documents generated for each patient can represent the patient's health history. The MyMedstories database 265 can be any type of storage medium including disk, tape, etc. In one embodiment, the MyMedstories database 265 is configured as a relational database containing a set of various tables used to store various types of information including user personal and profile information, MyMedstory documents generated for each patient, etc. The teachings of the present invention, however, are not limited to relational database structures and can equally apply to any other database or file structures including flat file structure, indexed file structure, hierarchical database structure, networked database structure, or combinations thereof, etc.

Figure 3:
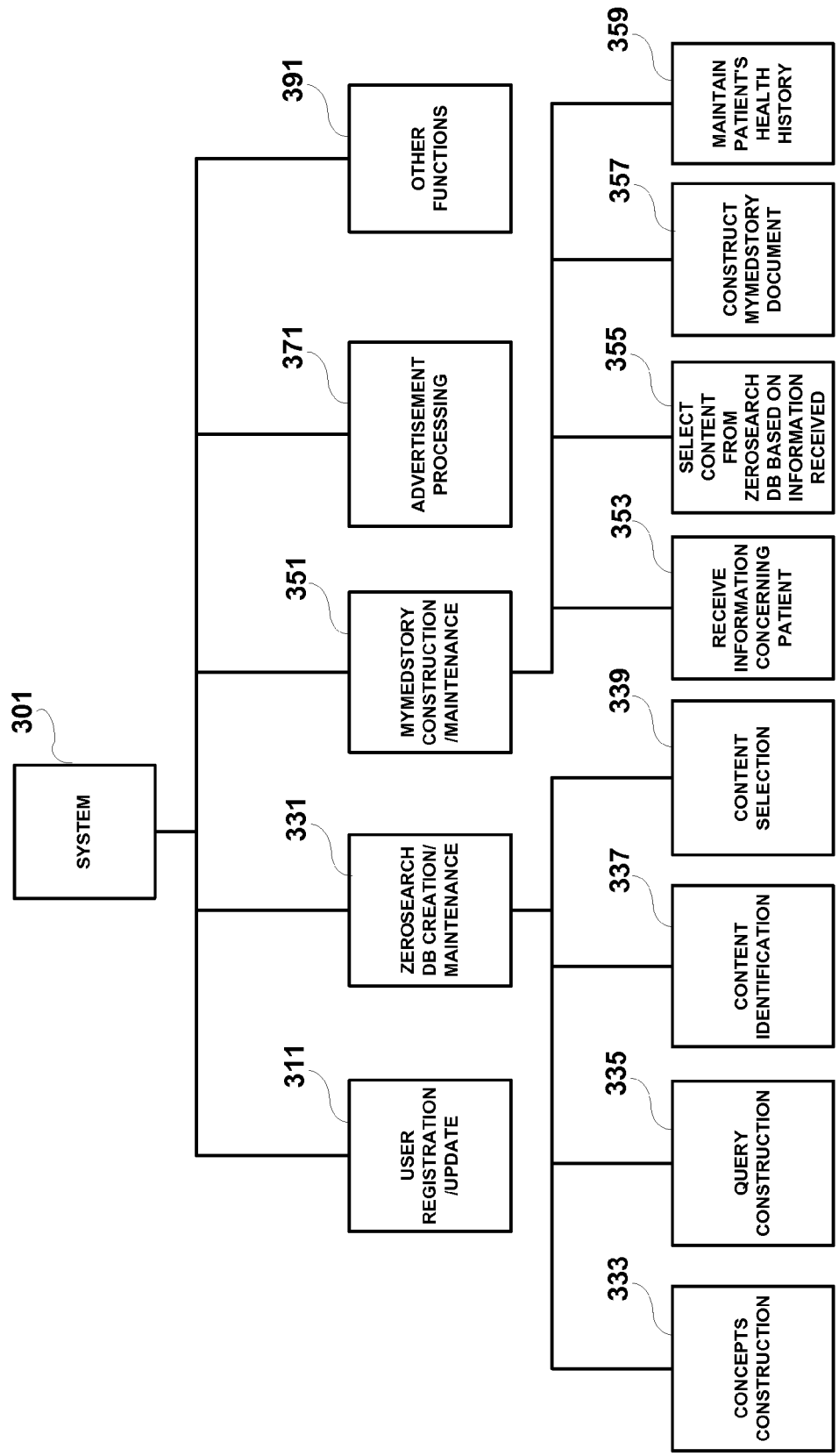
FIG. 3 is a functional block diagram of one embodiment of a system according to the teachings of the present invention.

FIG. 3 shows a functional block diagram of one embodiment of the system 201 described above with respect to FIG. 2. It will be recognized and appreciated by one skilled in the art that the following description is for illustration and explanation purposes and does not limit the scope of the present invention. In one embodiment, the logic and/or functions that are described below can be implemented using one or more programming languages suitable for the software or system development in a client-server environment, such as Visual Basic, C++ or Java, etc. It should be recognized by one skilled in the art, however, that the logic or functions described herein can be implemented by other programming languages, circuits, or techniques in accordance with the teachings of the present invention without loss of generality.

Continuing with the present discussion, the system 301 includes a user registration/update logic or function 311, a logic or function 331 for creating and maintaining the ZeroSearch database, a logic or function 351 for generating and maintaining the MyMedstory documents, advertisement/branding processing logic or function 371, and other processing logic or functions 391. The user registration/update logic 311 includes logic to allow the various users of the system to register with the system, to establish and maintain their user profile and identification information, etc. In one embodiment, the user profile and identification information may include the user personal and/or business contact information, unique identifier corresponding to the user, etc.

The ZeroSearch database creation and maintenance logic 331 contains logic to create and update various lists of content links associated with each code stored in the ZeroSearch database. The process of building and updating the ZeroSearch database is described in more details below. In one embodiment, the logic 331 contains concept construction logic 333, query construction logic 335, content identification logic 337, and content selection logic 339. The concept construction logic 333 is used to identify or determine one or more concepts (definitions) associated with each code stored in the database. The query construction logic 335 is used to generate a set of queries corresponding to the one or more concepts associated with each. The content identification logic 337 is used to identify a potential list of data sources or content links that may contain relevant information relating to the definitions or concepts associated with each code. In one embodiment, the identification logic 337 includes logic to search various databases available on the World Wide Web to identify a potential list of documents, content links, or data sources using the set of queries generated by the query construction logic 335. The content selection logic 339 includes logic to review the potential list of data sources identified by the content identification logic 337 and select therefrom a list of data sources to be stored in the ZeroSearch database, based upon various selection criteria including the quality and relevancy of the documents, ranking of the site or database from which the documents are retrieved, ranking or reputation of the sources of the documents, etc.

The logic 351, in one embodiment, includes logic 353 to receive and organize information about the patients received from the various sources including the healthcare providers, the healthcare provider organizations, the patients, etc., logic 355 to select the appropriate information (e.g., list of content links) from the ZeroSearch database corresponding to a set of queries generated based upon the information about the patients received from the various sources. The logic 351 further includes logic 357 to construct the MyMedstory document for the patient that contains the information retrieved from the ZeroSearch database. In addition, the logic 351 may include logic 359 to maintain a patient's health history by maintaining the patient's MyMedstories in the MyMedstories database.

Figure 4:
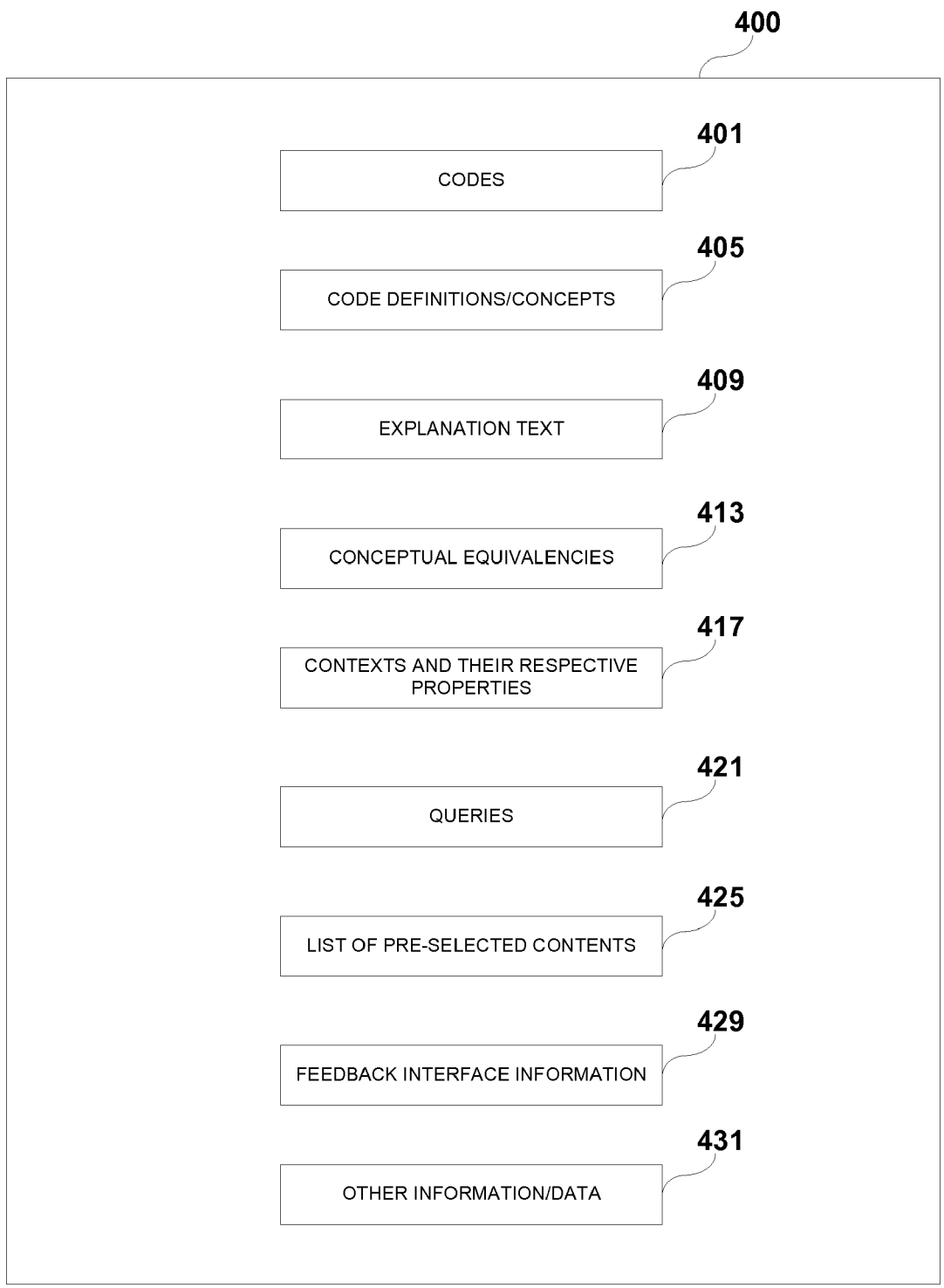
FIG. 4 illustrates a structure diagram of one embodiment of a database according to the teachings of the present invention.

FIG. 4 shows a structure diagram of one embodiment of the ZeroSearch database 261 described in FIG. 2 above. As illustrated in FIG. 4, the ZeroSearch database 261, in one embodiment, is configured to store code information and related information which include a list of codes 401. The codes 401 are described in more details below. For each code 401, the ZeroSearch database is configured to store a code definition or code concept 405, an explanation text 409, conceptual equivalencies 413 (also referred to as alternative, additional, supplemental or equivalent definitions herein), contexts and their respective properties 417, a set of queries based upon the code definition, the conceptual equivalencies, and applicable related or contextual information associated with each code, a list of selected contents or data sources associated with each code, feedback information, etc. The various types of information or data elements associated with each code are described in greater detail below. As explained above, in one embodiment, the ZeroSearch database 261 is implemented as a relational database structure and the various types of information stored in the ZeroSearch database 261 can be organized and maintained in various tables that can be cross-referenced or linked together using certain data items stored as keys or descriptors. The ZeroSearch database 261, however, is not limited to relational database structure and can be implemented in any other database or file structure including flat file, indexed file, hierarchical database, networked database, etc. or any combinations thereof.

Figure 5:
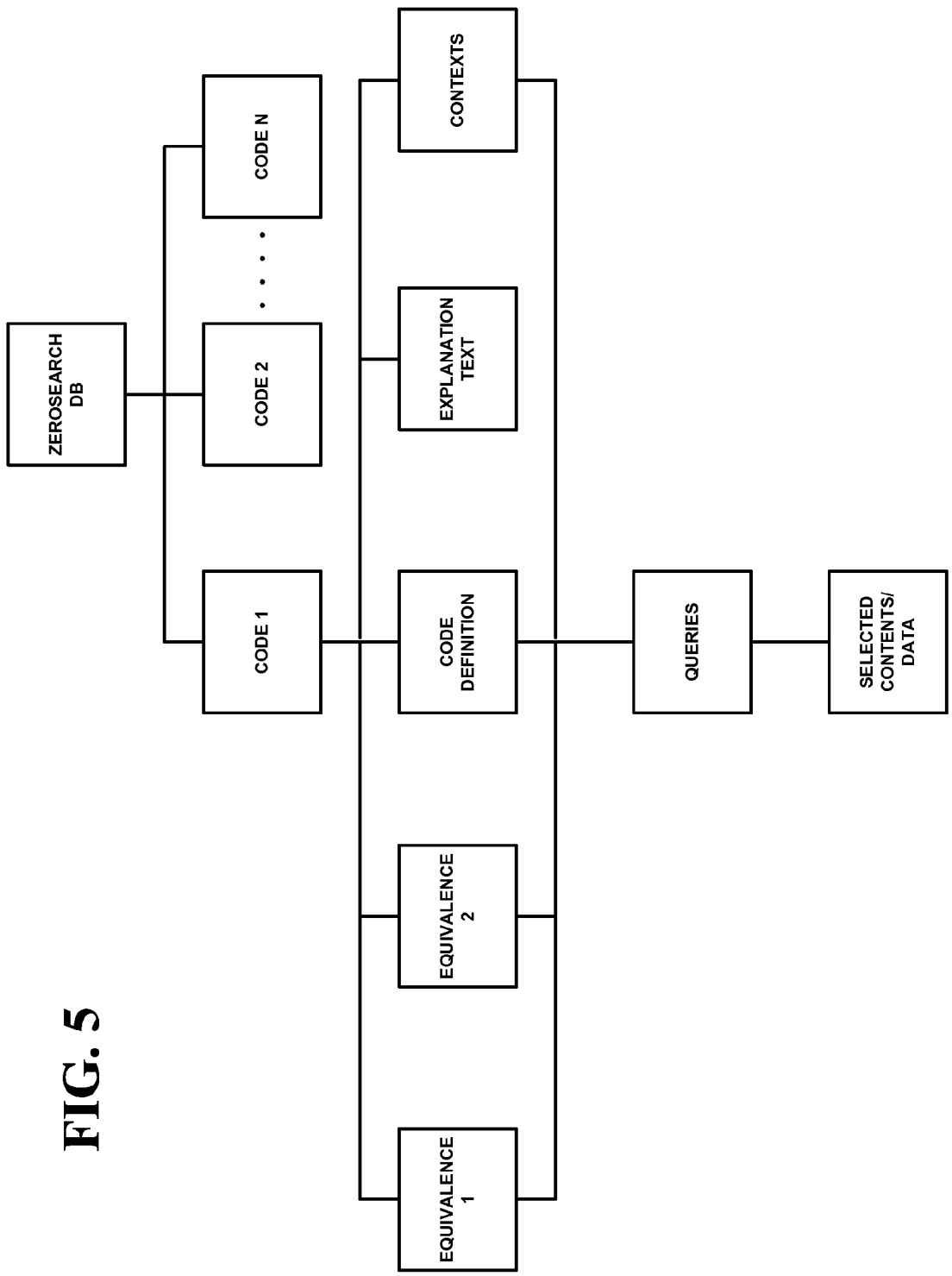
FIG. 5 shows a tree-view diagram of one embodiment of the database illustrated in FIG. 4.

FIG. 5 shows a tree view diagram of one embodiment of the ZeroSearch database 261 with respect to some of the information maintained therein. For example, a code identified as code 1 (e.g., one of the codes stored in the database 261) may have various types of associated information that are also stored in the database 261. As shown in FIG. 5, each of these types of information can be associated with the respective code using some identifiers, for example a unique code identifier or code number corresponding to the respective code. Each of the codes stored in the database 261, for example code 1, may have one or more code definitions and other information associated with it. For example, as shown in FIG. 5, code 1 has one corresponding code definition, one explanation text, one or more context fields, two alternative definitions or conceptual equivalencies, one set of queries constructed based upon the definition and the conceptual equivalencies corresponding to the respective code, and a list of pre-selected contents or data sources that are obtained using the corresponding set of queries. As described herein, the codes stored in the ZeroSearch database 261 may include the diagnosis codes according to the International Classification of Disease (ICD) that are used by the healthcare providers to report diagnoses, conditions, symptoms, signs, injuries, adverse drug effects, and other situations. For instance, the ICD-9-CM code "375.32" is used to indicate a condition or problem known as "Acute Dacryocystitis" (which is considered the definition or description of the code "375.32"). The alternative definitions or conceptual equivalencies of this code include, for example, "tear duct infection" and "tear sac infection". For this particular code, the following contextual information may be useful to identify more relevant and more targeted information regarding the condition/problem indicated by the respective code: (1) whether the patient is an infant, (2) whether the patient is a child, etc.

In one embodiment, a data source or content link associated with the code may be referenced by a file name or an address of a location at which the respective data source resides. In one embodiment, the data source can be referenced by a URL. The data source can contain text data, graphics data, voice data, video data, or any combination thereof.

Figure 6:
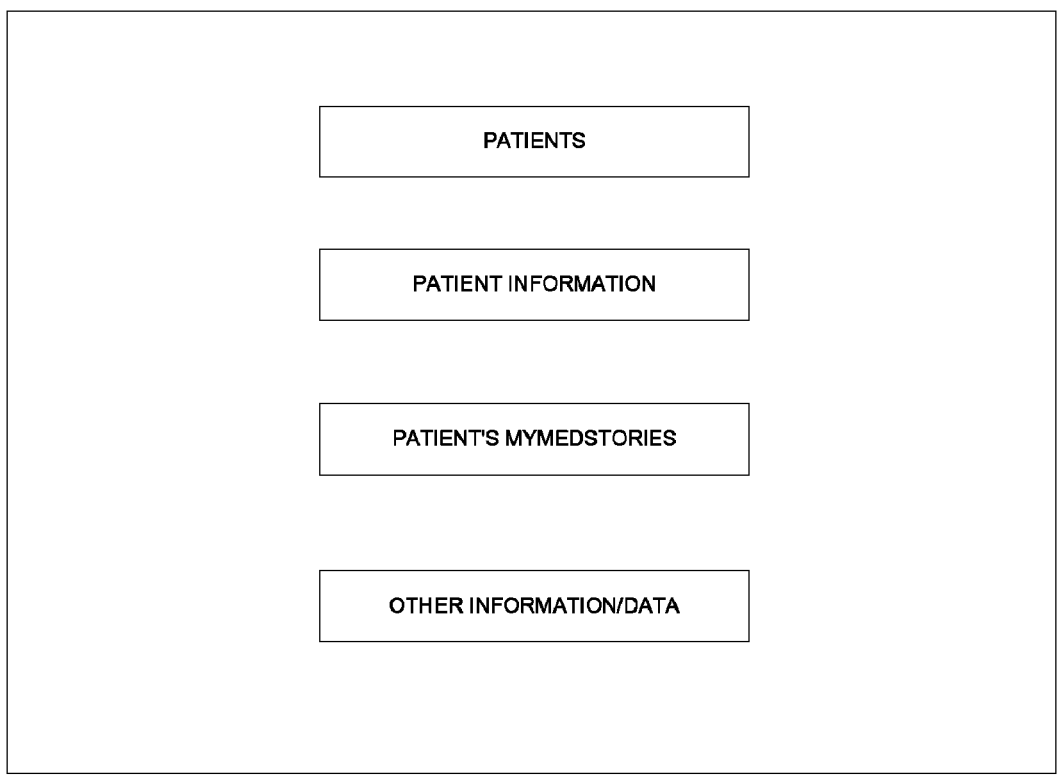
FIG. 6 is a structure diagram of one embodiment of a database according to the teachings of the present invention.

FIG. 6 shows a structure diagram of one embodiment of the MyMedstories database 265 described in FIG. 2 above. As illustrated in FIG. 6, the ZeroSearch database 265, in one embodiment, is configured to store the patient information and patient's MyMedstories generated by the system 201. In one embodiment, the database 265 may contain a list of patients that can be uniquely identified using some unique identifiers such as social security numbers, or unique user identifier assigned by the system, etc. Information about each patient such as patient personal information, profile, etc. may also be stored in the database 265. For each patient, the database 265 is also configured to store the MyMedstories generated by the system. The MyMedstories stored in the database 265 for each patient can collectively represent the patient's health history. Other types of information concerning the patients may also be stored in the database 265 including patient's benefit information, etc. As explained above, in one embodiment, the MyMedstories database 265 can be implemented as a relational database structure and the various types of information stored in the database 265 can be organized and maintained in various tables that can be cross-referenced or linked together using certain data items stored as keys or descriptors. The database 265, however, is not limited to relational database structure and can be implemented in any other database or file structure including flat file, indexed file, hierarchical database, networked database, etc. or any combinations thereof.

Figure 7:
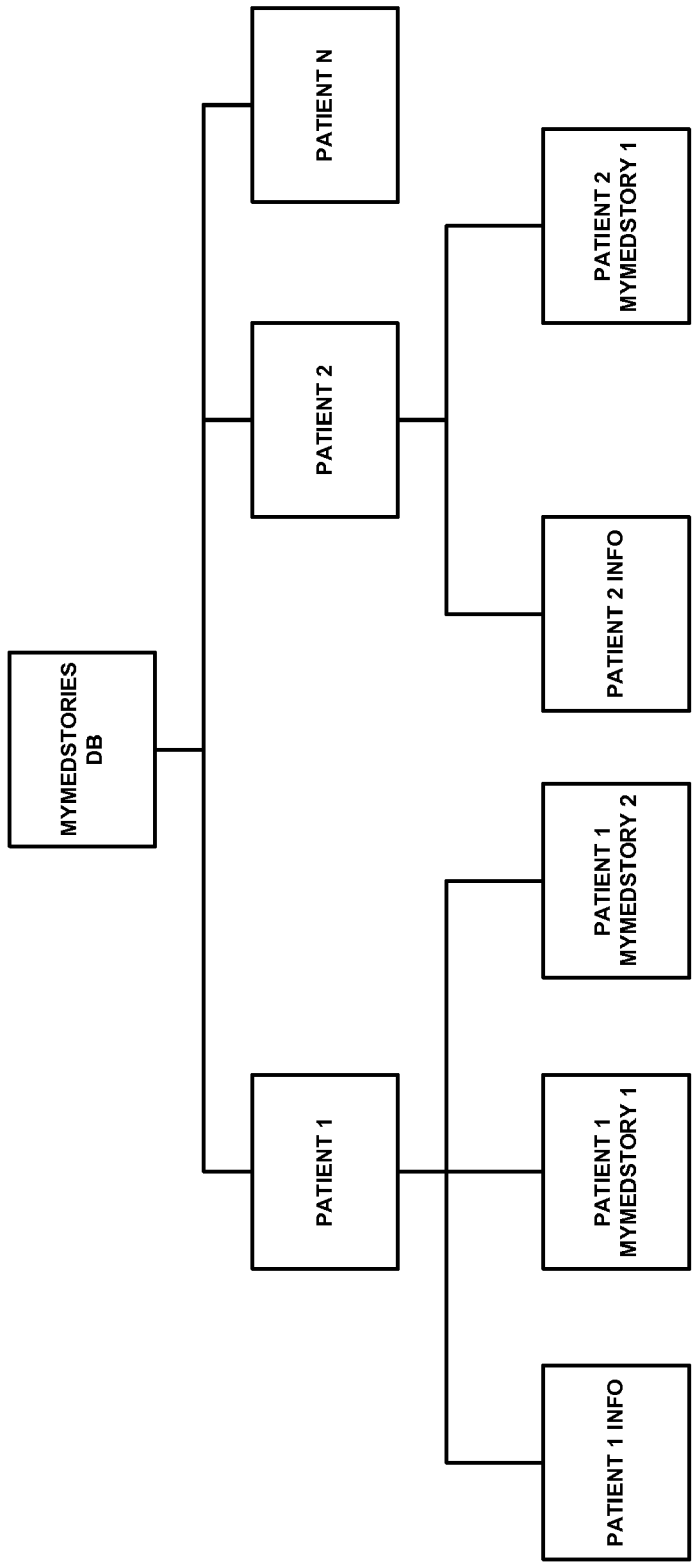
FIG. 7 shows a tree-view diagram of one embodiment of the database shown in FIG. 6.

FIG. 7 shows a tree view diagram of one embodiment of the MyMedstories 265 with respect to some of the information contained therein. In one embodiment, the database 265 is configured to store a list of patients and relevant information associated with each patient. The information associated with each patient stored in the database 265 may include the patient's personal and profile information, patient's identification information, etc. The patients can be uniquely identified by some unique identifiers such as social security numbers or unique user identifiers, etc. There can be multiple MyMedstories stored in the database 265 for each patient. For example, patient 1 has two MyMedstory documents that were generated by the system for him/her following his/her interactions or visits with the patient's healthcare provider. Accordingly, for each patient identified in the database 265, the patient's health history can be represented by the collection of the patient's MyMedstories stored in the database 265. The process of generating the MyMedstories for the patients following their interactions with their respective healthcare providers is described in more detail below.

Figure 8:
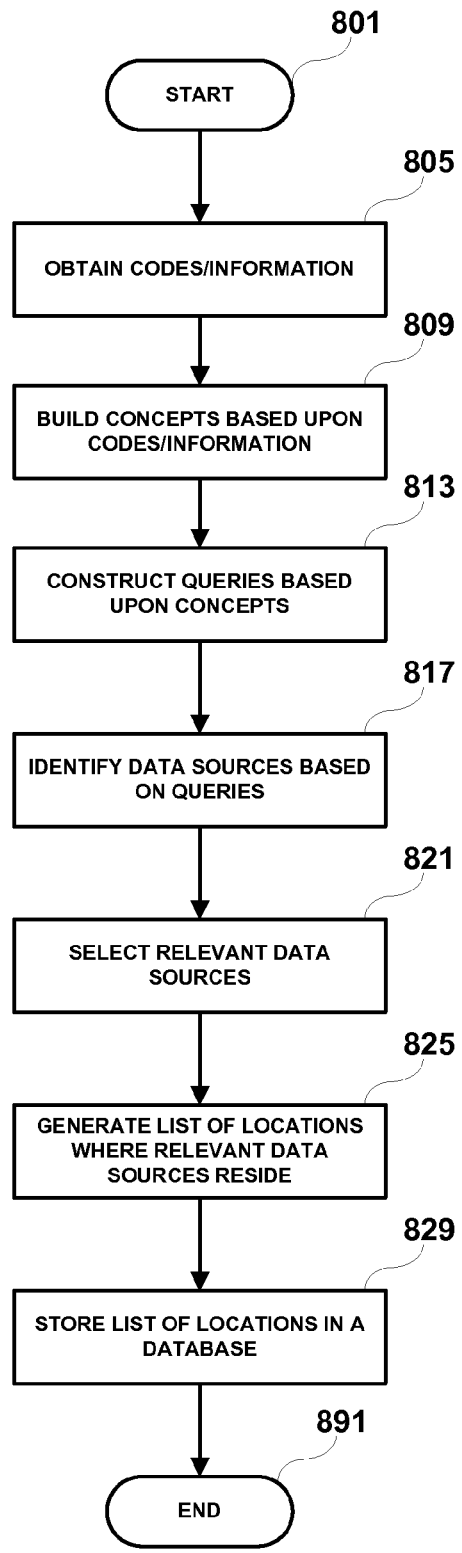
FIG. 8 illustrates a flow diagram of one embodiment of a method in accordance with the teachings of the present invention.

FIG. 8 shows a flow diagram of one embodiment of a process for building a ZeroSearch database. As mentioned above, the ZeroSearch database is a repository (flat file, hierarchical, relational, object-oriented, object-relational or distributed object-oriented databases as examples) of schema representing, for example, content documents, pages or URLs containing text, audio, video, images or any other media, chat rooms, newsgroups, communities and other Internet-based forums, that are associated with given codes and other information used in the health care delivery chain. The ZeroSearch database allows for the selection of highly pertinent documents, the access to which does not require any search on the part of the user.

As shown in FIG. 8, the process starts at block 801 and proceeds to block 805. At block 805, various codes and/or other types of information according to some classification schemes (e.g., International Classification of Diseases) are identified to be used for the building the ZeroSearch database. At block 809, various concepts/definitions/descriptions corresponding to the codes are determined. At block 813, a set of various queries is constructed based upon the concepts associated with each code. At block 817, various potential data sources or content links are identified using the queries constructed at block 809. At block 821, these potential data sources are reviewed for quality, relevancy, appropriateness, etc. and a subset of these potential data sources is selected therefrom. At block 825, a list of locations where the selected data sources reside is generated. The process then proceeds to block 829 to store the selected list in the database for the corresponding code. The process in FIG. 8 is described in more detail below.

It should be noted that various types of information (diagnoses, problems, procedures, drugs, tests and others) and codes can be used to build concepts. An example of such codes are codes from the ICD-9-CM classification of diseases, used by providers to report diagnoses, conditions, symptoms, tests, signs, injuries, adverse drug effects and other situations to insurance companies for reimbursement (see FIG. 16), or to other organizations as needed.

Code Concepts or Concept Representation

The following discussion can be applied to any diagnosis, procedures, laboratory tests, injections, materials and supplies, problems or other category of information that accompanies medical visits. For purposes of explanation and illustration, the discussion below is focused on the usage of ICD-9 (International Classification of Disease, 9th revision), or ICD-9-CM (International Classification of Diseases, 9th Revision, Clinical Modification, developed by the National Center for Health Statistics) codification of diseases, used to report diagnoses or problems to health care organizations (e.g., the insurance report shown in FIG. 16). The 10$^{th}$ revision of the ICD is also available. The ICD-10-CM (Clinical Modifications) is expected to be in use in the United States in 2001. ICD-10 is already in use in other countries.

The process described herein can apply to any of these classifications, as well as others including, but not limited to, CPT (Current Procedural Terminology) and HCPCS codes (HCFA Common Procedure Coding System), and READ codes (in the U.K.).

For any area of medicine or healthcare practice (e.g. Pediatrics, Obstetrics-Gynecology, Family Practice, Internal Medicine, etc.), the diagnosis (and other) codes can be turned into "concepts" as follows:

Conceptual Equivalencies

Each code's definition can be translated or expanded into a "concept" that represent its meaning in different forms. For example, code 466.1 corresponds to "bronchiolitis" in the ICD-9-CM classification. In its conceptual equivalence or alternative definition one may find "RSV" or "Respiratory Syncytial Virus", a major cause of "bronchiolitis". Another example is "Gastroenteritis" that is represented by code 009.0, also commonly called "Stomach Flu". "Stomach Flu" becomes part of the concept associated with the ICD-9-CM code 009.0. This translation into a richer concept is used for the construction of the ZeroSearch database. Terms used in the ICD-9-CM or ICD-10 classifications are often not used in non-medical settings where they do have equivalent or alternative terms to represent them.

Contexts or Contextual Information

Each type of information, code, equivalence or other data may be associated with one or more "contexts" to characterize it further. For example, "sex" may be important with respect to "UTI" or "Urinary Tract Infection", code "599.0". Each code may be associated with one or more values for contextual information (e.g., Child, Male, Asthma, etc.). Contexts can be defined or implemented as any structure (for example, a simple term, a database scheme, an object, a concept or other). In one embodiment, if there is more than one context, they can all be ranked by level of importance or weight. The definition of contexts may contain additional properties. Any specific algorithms can be implemented to take such properties into account when using the database to derive ZeroSearch contents in a particular situation. In addition, contexts may be associated with operational definitions. For example, infant may be defined by 0<age<1 year old. Operational definitions may include other codes. Contexts may also point to specific documents or services. For example, code "034.1" for "Scarlet Fever" may have a context named "Compliance" to which may be attached a text, a URL, graphic or executable program to emphasize the need to comply fully with the 10 consecutive days of antibiotics course required, even though all symptoms may have already disappeared after only a few days of antibiotherapy.

Conceptual Queries

The resulting database or list of code concepts allows for the formulation and execution of conceptual queries against any type of database. The discussion in this example refers to web-based databases.

Consider a database site called "XYZMed" accessible using the following URL: http://www.XYZMed.com/cgi-bin/search?queryText=.

Using the code concepts defined above, one can construct a series of queries into the database. For example, code ICD-9-CM "375.32" may be associated with the following concept:

Code: 375.32

Name or Definition: Acute Dacryocystitis

Equivalencies: "tear duct infection", "tear sac infection"

Context: infant, child

For each name, version of the name, or equivalence, a query is generated as well as queries augmented with contextual information. If contexts are non-exclusive, there will also be combinations of contexts. For the example above, the resulting queries may include the following:

http://www.XYZMed.com/cgi-bin/search?queryText=Acute+Dacryocystitis
http://www.XYZMed.com/cgi-bin/search?queryText=Acute+Dacryocystitis+infant
http://www.XYZMed.com/cgi-bin/search?queryText=Acute+Dacryocystitis+child
http://www.XYZMed.com/cgi-bin/search?queryText=Dacryocystitis
http://www.XYZMed.com/cgi-bin/search?queryText=Dacryocystitis+infant
http://www.XYZMed.com/cgi-bin/search?queryText=Dacryocystitis+child
http://www.XYZMed.com/cgi-bin/search?queryText=Tear+Duct+Infection
http://www.XYZMed.com/cgi-bin/search?queryText=Tear+Duct+Infection+child
http://www.XYZMed.com/cgi-bin/search?queryText=Tear+Duct+Infection+infant
http://www.XYZMed.com/cgi-bin/search?queryText=Tear+Sac+Infection
http://www.XYZMed.com/cgi-bin/search?queryText=Tear+Sac+Infection+child
http://www.XYZMed.com/cgi-bin/search?queryText=Tear+Sac+Infection-infant In this example, the above queries are direct http queries. However, any type of query can be supported, with a different syntax (e.g. Tear+and+Sac+and+Infection+and+infant"), different logical operators (e.g. "or"), different access methods (e.g. an HTML form), or other modalities.

Searching for web documents using only the ICD-9-CM or ICD-10 definition is not sufficient. Indeed, many diagnoses, conditions or problems are represented differently in non-medical settings. Thus, switching from the original definition to a richer conceptual representation allows for effective and efficient queries in a large variety of databases. For example, "Dacryocystitis" might not yield any document in a pediatrics database, whereas "Tear Duct Infection" might.

As an additional example, a search for "Gastroenteritis" (code "009.0") may yield on average less or different answers than the equivalent popular description of "Stomach Flu".

Content Identification and Selection

To each of the conceptual queries is then associated a list of contents or data sources that are identified in a specific database using the corresponding query. The review and selection process to select appropriate documents or data sources to be included in the ZeroSearch database, while "manual" in nature, could be replaced or enhanced by algorithmic techniques. The quality and relevance of each query is assessed and a resulting set of identified documents is selected. The selection process can be manual, by reading the document and assessing their quality. It could also use automated algorithms, or involve other criteria such as ranking of the site or database where the document resides, ranking of the source of information, etc.

If there are adequate documents using any of conceptual queries for a particular code, with or without contextual information, they can be selected with their respective contexts to which weights may also be assigned.

For example, the query:

http://www.XYZMed.com/cgi-bin/search?queryText=Bronchiolitis may yield a document "A" that is deemed useful (manually or by other methods). "A" is then added to the ZeroSearch representation for the ICD-9-CM Code Concept "466.1". The URL for "A" may look like: http://www.XYZMed.com/A.

http://www.XYZMed.com/cgi-bin/search?queryText=Respiratory+Syncytial+Virus+Infant may yield a document "B" that is deemed useful. "B" is then added to the ZeroSearch representation for the ICD-9-CM Code Concept "466.1", along with the site (XYZMed) and the context "Infant".

Hence, the ZeroSearch database may contain, for example:

For each ICD-9-CM code (or other code):
  The code
  The code definition
  An explanation text (e.g. "Disease D is a common disease in infants.")
  The Conceptual Equivalencies
  The Contexts and their respective properties (e.g., weights)
  A set of queries into various databases or sites
  A list of pre-selected contents or data sources annotated with contexts and their weights and other properties if any.
  A Feedback Interface Information
  Other information Accordingly, ICD-9-CM codes can thus be transformed into objects with the above properties. Classes of codes and their conceptual representation can be created, as well as functions and methods operating on them.

The above list of fields or properties is not exhaustive and is extensible. It can be enhanced with many more aspects of any "Code Concept". For example, a property could be reserved for "Therapeutic Management" information. In the case of a CPT code for a procedure, a property could be reserved for "Preparation". In the case of an NDC code for a drug, a series of properties could address drug-related properties.

The content associated with any ICD-9-CM code, after selection, can be represented as a tree structure, where each link represents a different context associated with the code under consideration. If a particular context applies when matching patient information to the information in the database, then the content it points to can become a candidate for inclusion in the service delivered to the patient or consumer.

Figure 9:
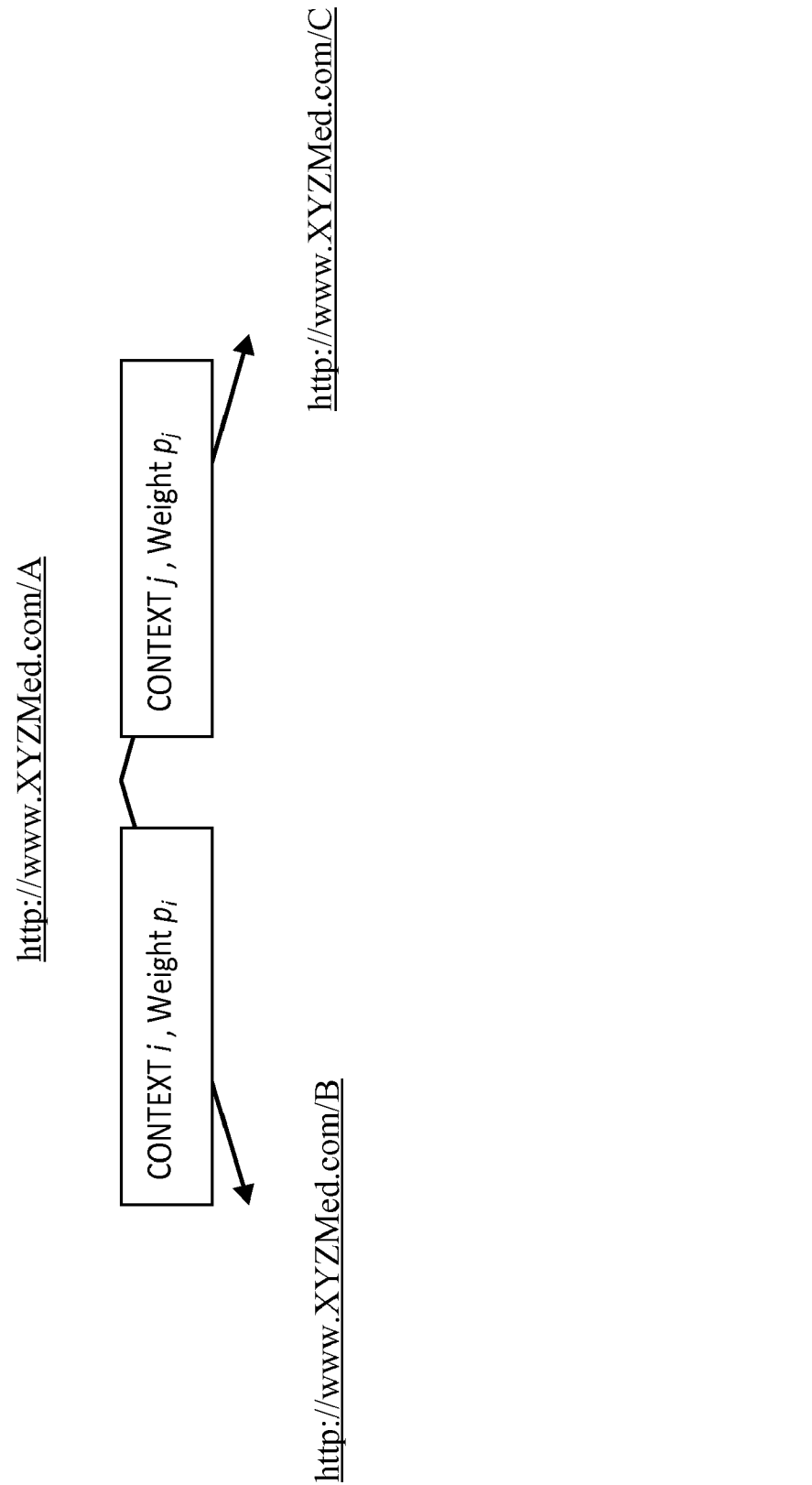
FIG. 9 illustrates exemplary ZeroSearch links for a given ICD-9-CM code according to an embodiment.

For instance, exemplary ZeroSearch links for a given ICD-9-CM code are illustrated in FIG. 9. In this example using ICD-9-CM codes, each code is transformed into a concept code leading to conceptual queries and the subsequent construction of such a "tree".

The database can be stored in any format and any query language or program can be used to query schema information from the database, including but not limited to Java, Java script, Java applets, HTTP servlets, IIOP, CGI, or SQL.

The Feedback Interface Information property may be used to create feedback mechanisms about the selected database information relating to the specific condition. The nature of the interface may change according to the various implementations.

Drug Concepts

A ZeroSearch Database can also be built on the topic of prescription or OTC drugs, using, for example, the NDC classification (National Drug Codes) but also other descriptions including but not limited to trade or generic names.

The process is similar to the one described above for conditions. The list of sites or databases to consider may be different. A context can be associated to each drug as well, and the same type of trees can be built.

Laboratory Tests, Procedures, Materials, Supplies, Injections Concepts

A ZeroSearch Database can also be built on the topic of laboratory tests, procedures, materials, supplies or injections, as well as any other types of information that may be involved in medical care which may or may not have corresponding codes.

The process is similar to the one described above for conditions. The list of sites or databases to consider may be different.

Feedback

MyMedstory documents can be used to provide feedback information from the patient on any matter relevant to the document. Examples of feedback information include, but are not limited to, drug tolerance, wellness or treatment effectiveness.

Feedback can also be provided regarding the content of the ZeroSearch links. Users can thus express preferences and other evaluation criteria or information. Part of the information which can be used to design the feedback mechanism (for example a pull-down menu) can be stored in the conceptual definitions of codes or other information.

Figure 10A:
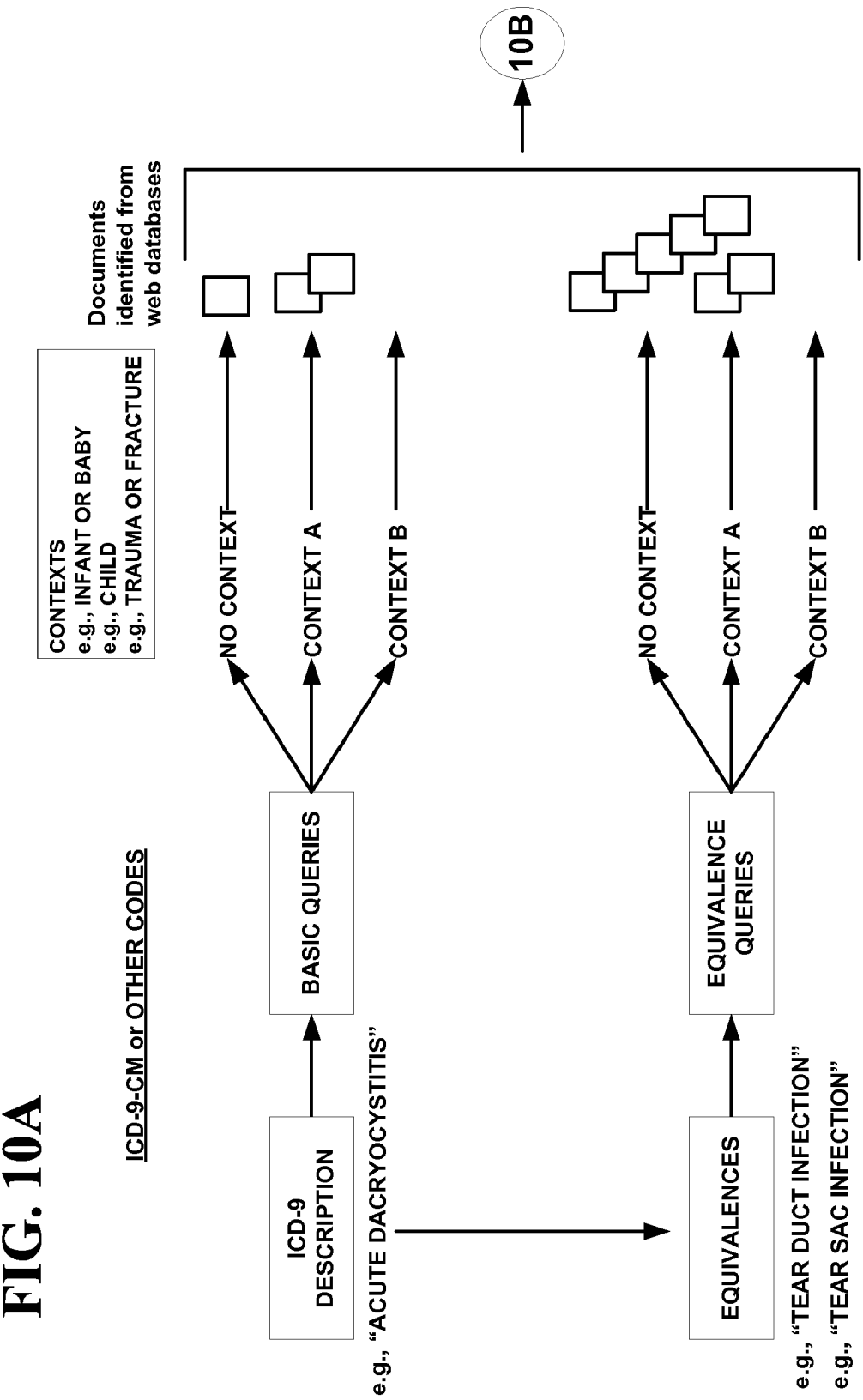
FIGS. 10A and 10B show a block diagram of one embodiment of a method according to the teachings of the present invention.
Figure 10B:
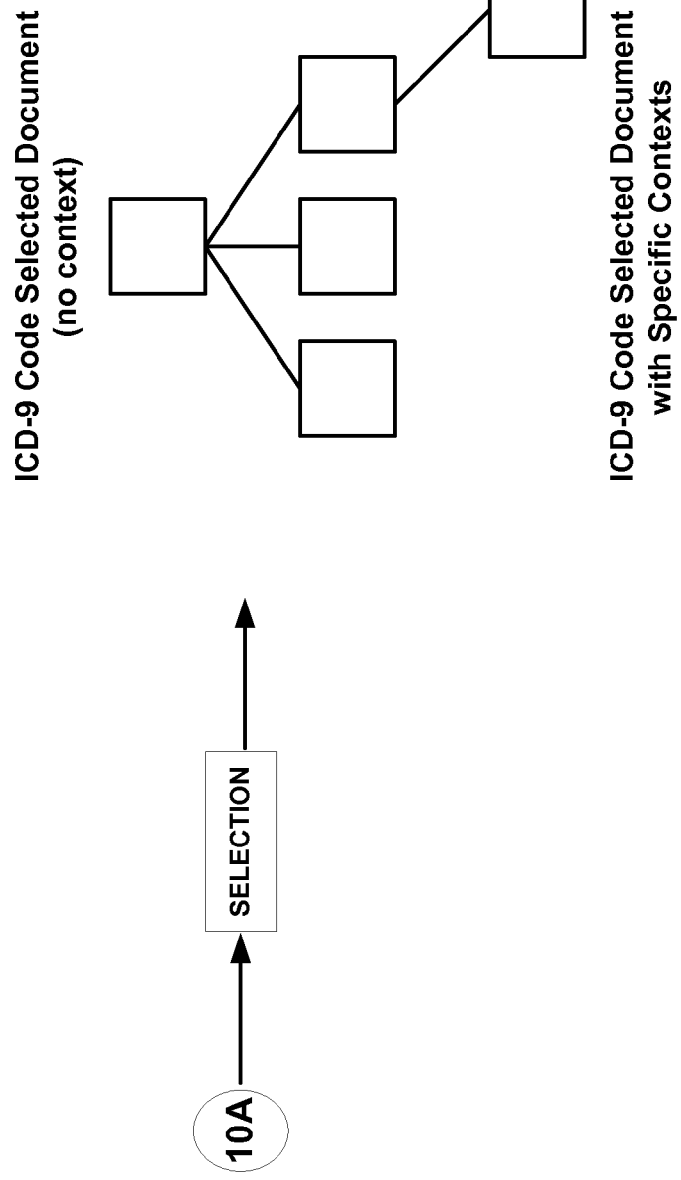

FIGS. 10A and 10B illustrate a block diagram of one embodiment of a process for building the ZeroSearch database as described above with respect to FIG. 8. As shown in FIGS. 10A and 10B, an ICD code may have one definition (e.g., "Acute Dacryocystitis" in this example) and multiple alternative definitions or equivalencies (e.g., "Tear Duct Infection" and "Tear Sac Infection"). The basic queries are constructed based upon the definition associated with the given code. Likewise, the equivalence queries are constructed based upon the alternative definitions or equivalencies associated with the given code. As shown in FIGS. 10A and 10B, some of the queries constructed may then be augmented with applicable contextual information to generate queries having contextual information as part of the query criteria. The various queries are then used to perform search into various web databases to identify documents or data sources that match the query criteria specified. These potential data sources are then reviewed and a subset of these may be selected based upon various selection criteria to generate a list of data sources to be included in the ZeroSearch database for the given code.

Figure 11:
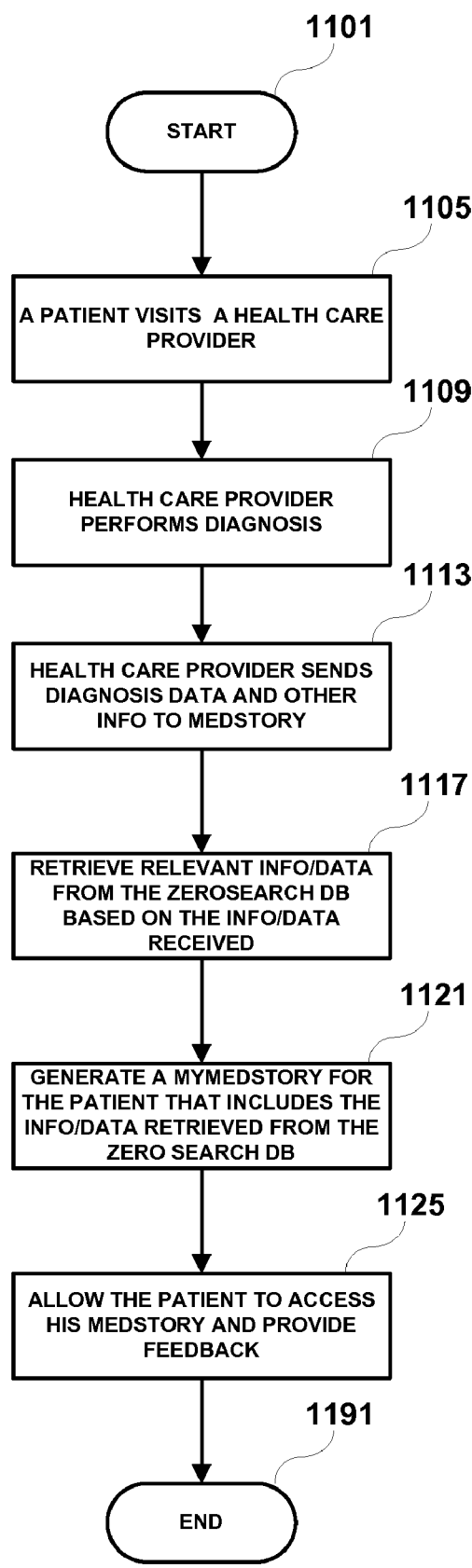
FIG. 11 is a flow diagram of one embodiment of a method according to the teachings of the present invention.
Figure 12:
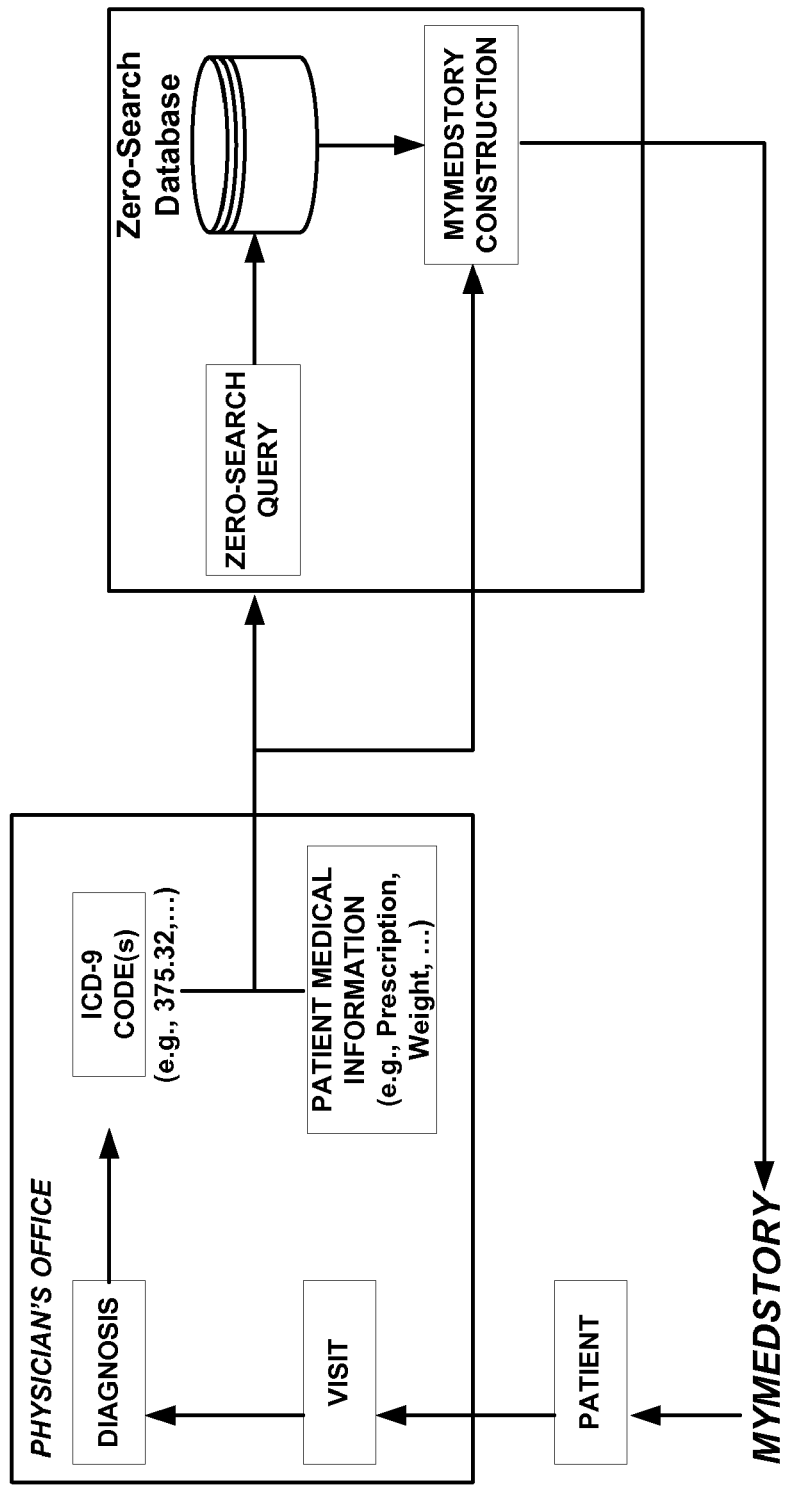
FIG. 12 illustrates a block diagram of one embodiment of a method according to the teachings of the present invention.

FIGS. 11 and 12 show a flow diagram and block diagram, respectively, of one embodiment of a process for generating a MyMedstory for a patient following an interaction between the patient and a healthcare provider. At block 1105, a patient visits a healthcare provider. At block 1109, the provider performs a diagnosis. At block 1113, the healthcare provider sends diagnosis information and other appropriate information to the Medstory system. The diagnosis information may include diagnosis codes and other types of information including tests, procedures, injections, materials and supplies, etc. Other types of information may include patient medical information such as gender, age, weight, height, prescription, etc. At block 1117, the information about the patient received from the healthcare provider is used to retrieve from the ZeroSearch database appropriate information (e.g., a list of data sources) that corresponds to a set of queries constructed or selected based on the information about the patient provided by the healthcare provider and other sources. At block 1121, a MyMedstory document is generated which contains the information retrieved from the ZeroSearch database. At block 1125, the patient is allowed to access, via the Internet or other methods of communications, the MyMedstory generated for him. The patient is also allowed to provide feedback to the system using one or more interfaces provided to him by the system which can be in various forms depending upon the particular implementations of the present invention. The process shown in FIG. 11 is described in more detail below.

In one embodiment, the construction of a MyMedstory document involves different interactions between different entities or sources, databases and other components of the system. Some information may not be obtained immediately, such as benefits-related information. Thus, the system may receive information from different entities at different times. When information about the patient is available following an interaction between the patient and the provider, the system then uses the patient's information available to query the ZeroSearch database to retrieve relevant information and generates a MyMedstory document for that patient.

The MyMedstory document can be constructed in any language, including, but not limited to HTML and XML, and support various types of extensions, plug-ins or other technologies. As an example, handheld devices may require use of other languages such as WML (Wireless Markup Language). Other specifications or protocols would be used to describe MyMedstory in a television or set-top environment, or other environment.

Sources of Information

As mentioned above, various sources and entities may provide various types of information and data that can be used by the system to generate a MyMedstory document for a patient. These various entities may include the healthcare providers, the IPA, medical group or other provider organizations, the health plan, insurer or health care organizations, government organizations, and the patient himself, etc.

Transmission of Information from the Physician or Provider

Information about the patient can be transmitted to the system by any acceptable means, including phone, fax or via the Internet/world-wide web or other networks. Internet connections can use secure http (https) and other technologies and policies as needed to provide the necessary security, confidentiality and privacy.

Patient Profiles

The system described herein allows self-reported profiling information from the patient. Transmission of this information may be performed using different communications means, including but not limited to telephone, Internet, fax, etc.

Patient Information

Patient personal and related information may be received from the physician's office or any other source in the health care delivery chain. The patient information may include the following:

Patient name/ID/address

Patient DOB (Date of Birth)

Sex/Gender

Health Plan Information

Provider Association Information

Diagnosis information and other types of information about the patient can be transmitted to the system. Such information may include the following:

ICD-9-CM Diagnosis Codes, NDC Codes and/or drug names, etc.

Other Codes

Low resolution medical information (e.g. weight, height, blood pressure, etc.)

Prescription information for prescription drugs and over-the-counter drugs, materials, supplies or other physician-provided information or recommendations (e.g. counseling, education, diet, exercises, or other therapeutic services)

Comments from the Physician Provider (in any format including text, video, audio, etc.)

Other types of information (e.g. vaccinations, procedures, pre-conditions, risks) can be included as well.

Provider Information

Information provided to the system may include:

Provider Name

Provider ID

Phone number

Office visit date

Other provider information

ZeroSearch™ Content

In one embodiment, when the information about a patient is available, the ZeroSearch database can be used to determine which ZeroSearch content to include in that patient's MyMedstory. As described above, the ZeroSearch content may be relevant to any aspect of the information provided about the patient (e.g., diagnosis codes, prescription drugs, non-prescription drugs, tests, and others).

In one embodiment, the MyMedstory document makes uses of a certain number of ZeroSearch links to provide information on diagnoses, procedures, drugs and other matters for the patient. If that number is less than the number of sites for which the database has ZeroSearch links for the particular code, then a site ranking mechanism may be used to select, for example, five sites to be represented. Sites can be web-based sites, medical or not, informational, e-commerce or any other content repositories.

In one embodiment, site rankings may be based upon various criteria including the result of editorial choices, the patient's health plan (if the company or organization maintains a relevant information database), preferences or feedback information from previous interactions with the patient, preferences from the provider, and other factors that may be included. Site rankings may be determined or modified manually or using algorithms and automated methods.

In one embodiment, content links may be referenced by specific addresses corresponding to locations where the content sources reside. In the world-wide-web context this may be represented by a URL, a CGI query, a form or other methods of representation.

Figure 13:
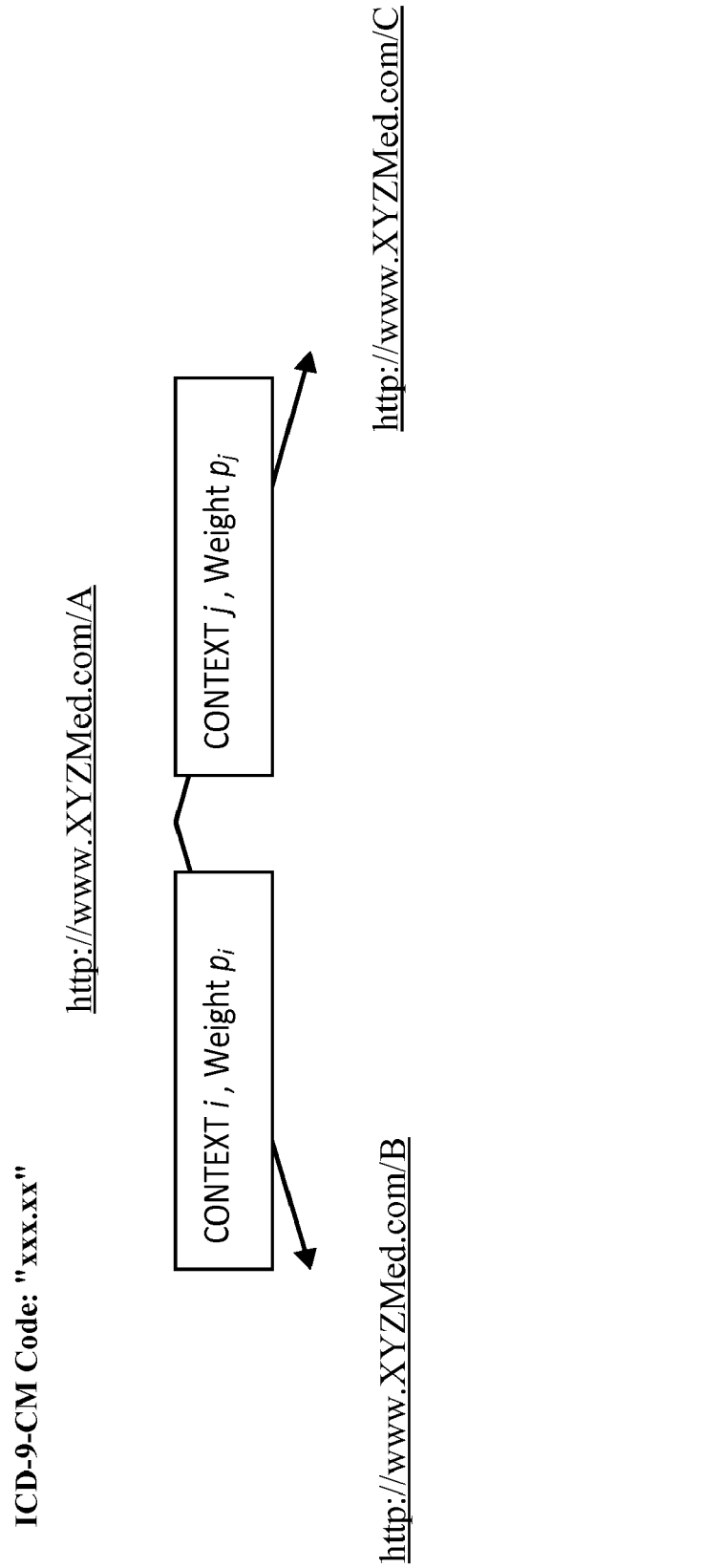
FIG. 13 illustrates an exemplary "tree" in the ZeroSearch database for a particular ICD-9-CM Code according to an embodiment.

As an example, referring next to FIG. 13, consider a "tree" in the ZeroSearch database for a particular ICD-9-CM Code called "xxx.xx".

In one embodiment, the matching process to select appropriate content links for the patient can be performed as follows:

If the only information provided on the diagnosis is the code "xxx.xx", and no context is determined, then the ZeroSearch link that will appear on MyMedstory, for the site "XYZMed.com" will be: http://www.XYZMed.com/A If one of the two contextual information can be determined then the ZeroSearch link that will appear on MyMedstory, for the site "XYZMed.com" will be: http://www.XYZMed.com/B, or http://www.XYZMed.com/C.

In one embodiment, if the two contextual information can be determined, then the ZeroSearch link that will appear on MyMedstory, for the site "XYZMed.com" will be the link associated with the context that has the highest weight. If weights are equal, a strategy such as using the first one can be used. In another embodiment, both links will be presented to the patient.

Other algorithms can be designed to search the trees of links. The nature of the contexts and weights could vary as well.

If a code has no associated ZeroSearch links in any sites according to the ZeroSearch database, the parent code can be used as a substitute. For example, if code "034.1" for "Scarlet Fever" is not in the database, the parent code "034" for "Streptococcal sore throat and scarlet fever" is then looked up.

Health Plans

Information from the patient's health plan may include all available information on the patient's record, including but not limited to explanations of benefits, referral services, etc. Information regarding the current condition and associated benefits or intervention programs may be included as soon as it is available.

The information can be made available by direct connection into the proper database or by connecting via another interface.

Provider Organizations

The provider organization that the physician belongs to may also have information relevant to the patient. It might be tracking local health data and news, provide community health news, and other functions.

Provider Organizations may also have their own campaign or intervention program equivalents to increase the quality of care and reduce costs.

The information related to those organizations can be made available by direct connection into the proper database or by connecting to an existing interface.

Providers

Physicians and other health providers (dentists, etc.) can use the Medstory system to communicate with health care consumers in various ways (e.g. specific information, newsletters, appointment scheduling and others).

Laboratories

MyMedstory can be used as a vehicle for pertinent and targeted messages from other organizations. This includes clinical laboratories and pharmaceutical entities.

Other Organizations

MyMedstory can be used as a vehicle for pertinent and targeted messages from other organizations. This includes, for example, public health organizations.

On-line Drugstore and ZeroSearch

If the patent uses an on-line drugstore, MyMedstory may use the information available to obtain information from the on-line drugstore and display the relevant information to the patient or consumer. It may thus provide the patient with a link in the drugstore's site to the specific prescription or non-prescription drug that has been recommended by the provider, without the need to perform searches. The availability of drugs and refills from the drugstore can also be accessed from the MyMedstory document.

On-line Drugstore, Comparisons and ZeroSearch

An additional way to provide ZeroSearch electronic commerce services can be to direct the user to the on-line drugstore of choice, as determined, for example, by a price comparison algorithm. The user is presented with several ZeroSearch options (direct to the page of the item in question), ranked by increasing price. Other ranking criteria could also be used.

Therapeutic and Disease Management

Specific information on the course of the recommended treatment may be included to help patients manage their therapy. These targeted messages may be contributed by various sources including health plans, providers, provider organizations, governmental agencies, health agencies, etc.

For example, Code "034.1" for "Scarlet Fever" can have a field or property named "therapeutic management" which may contain the following data: "Symptoms may disappear in the first few days. However, it is essential that you DO NOT STOP the treatment until it is over, as prescribed by your physician".

The availability of drugs and refills from the drugstore can also be accessed from the MyMedstory document.

Advertising/Branding

Advertising/branding may be added to MyMedstory. Since MyMedstory is patient specific, advertisements or branding can be highly targeted. For example, a health plan of a given patient can present new benefit information or programs to their members in a targeted fashion.

Other Services

Other services may be added to, or integrated into the MyMedstory, including, but not limited to, health risk assessment, health tracking and calendar (e.g. pregnancy course), e-commerce services. The integration can be done through any application programming interface (API) or any other mechanism.

The MyMedstories Database

Each MyMedstory constructed can have a unique identifier and can be stored in a database. As described above, the MyMedstories database is a repository (flat file, hierarchical, relational, object-oriented, object-relational or distributed object-oriented databases as examples) of schema representing individual MyMedstory documents. Queries can be made via any query language or program.

Longitudinal MyMedstory Content

Figure 14:
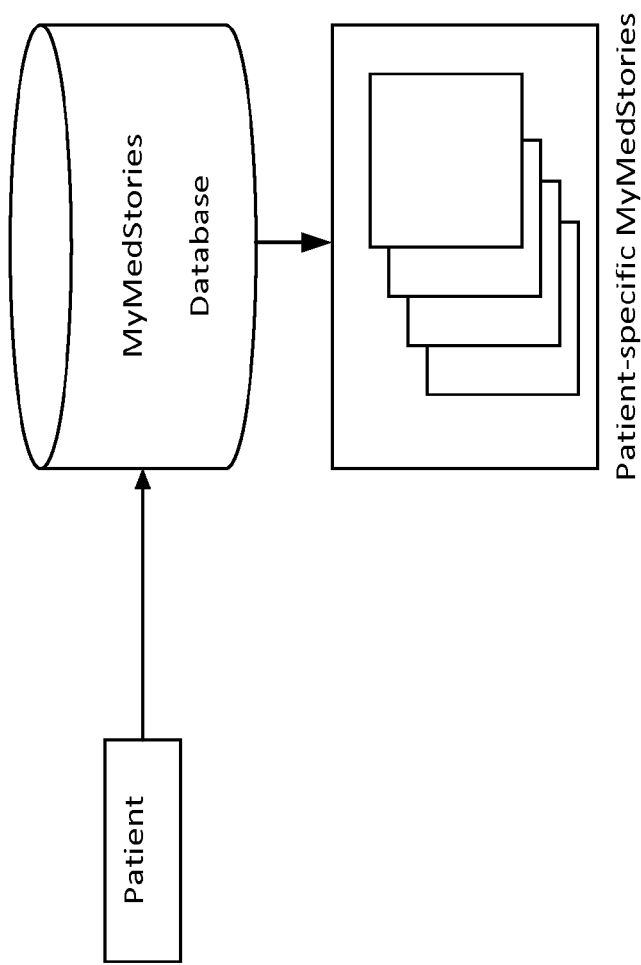
FIG. 14 is an exemplary diagram illustrating how a MyMedStories Database facilitates access to patient information according to an embodiment.

Referring next to FIG. 14, an exemplary diagram illustrating how a MyMedStories Database facilitates access patient information is provided. A direct consequence of the existence of this database is the ability for each consumer (or each authorized user, which may also include the provider) to access any of his past MyMedstory documents. The collection of personal MyMedstory documents, called MyMedstories, can represent a record of one's health history.

For example, parents can quickly return to records of conditions that have affected their child or children in the past, or obtain a list of vaccinations. Similarly, any user can go back to past prescriptions or recommendations from his physicians.

In addition, the MyMedstories database can be queried using any criteria. For example, one could retrieve all episodes of infectious diseases, or episodes for which an antibiotic was prescribed, or episodes when no drug was prescribed.

Furthermore, other modules can be added which will operate on the data from a set of MyMedstory documents. For example, a module may take information from MyMedstory documents such as "weight" and "height" and reconstruct a "growth curve" plot that can be viewed by the child's parent or guardian.

Dynamic MyMedstory Content

MyMedstory documents can be modified over time. For example, benefits information may be added to the document as they are generated by the health plan. This may possibly take place after another subsequent visit to the physician has already occurred, for which another MyMedstory was generated. In another example, the document may contain specific services related to therapeutic management and may keep the patient informed of key dates, appointments or other functions.

Another form of service may be a news service, specifically focused on news related to present or past conditions. The news can be presented in the context of relevant past or present MyMedstory in the database. For example, if a patient was diagnosed with an "Ovarian Cyst", a news application can select a news relevant to this matter. It can then inform the patient, either proactively by an alert mechanism of any type, or passively when the patient returns to the specific MyMedstory or to his MyMedstories personal repositories.

Hence, a MyMedstory document is a "dynamic" document undergoing changes as new information is acquired by a variety of means.

MyMedstory: Targeted Health Intervention

As mentioned above, MyMedstory can act as a delivery vehicle for important health-related messages that health care organizations or provider organizations would like their patient members to receive, including information related to "Intervention Programs".

If the Health Plan of the consumer has specific campaigns or intervention programs in place, they can be mentioned in or make direct use of the MyMedstory to communicate important and targeted information from those programs.

For example, communications about vaccinations may be provided to parents of newborns and infants; communications on the importance of regular doctor visits for pregnant women may be provided to increase detection of high-risk pregnancies; communications about enrollment in specific intervention programs may be provided to selected patients, etc.

In all cases, the specificity of MyMedstory can represent a means to deliver targeted, focused and relevant information to the patients, regarding their current condition or other aspects of their health.

Modules can be added to, or integrated into, the system that will choose the most appropriate health plan intervention program in accordance with the patient's specific context. This may include the ICD-9-CM code but also age, sex and any other variable or data present in the MyMedstory document or in the longitudinal history of MyMedstory documents (MyMedstories).

FIGS. 15A, 15B, and, 15C illustrate an example of one embodiment of a web user interface for presenting a MyMedstory document to a patient that includes personalized health-related information and links to other sources of relevant information, as described above. As shown in these figures, the MyMedstory generated for a patient following his interaction with his provider may include the following: patient and provider identification; the specific conditions, problems or other aspects of the patient's health based on the information about the patient received from various sources; prescription information and notes; list of content links or data sources retrieved from the ZeroSearch database from which the patient can access additional information relevant to his situation; links to various web sites including drug stores, etc.; mechanism to allow the patient to provide feedback to the system; and mechanism to allow the patient to access his collection of his past and present MyMedstories, etc.

FIG. 16 shows an example of insurance report containing codes according to the International Classification of Disease (ICD). As shown in FIG. 16, various diagnosis codes (ICD-9 codes) are included in this form that can be used to indicate the results of the provider's diagnosis (i.e., indicating the patient's problems and/or conditions). In addition, this form can also be used to include other types of information including description of the nature of the visit, laboratory information, procedures, materials and supplies, injections, etc.

The invention has been described in conjunction with the preferred embodiment. It is evident that numerous alternatives, modifications, variations and uses will be apparent to those skilled in the art in light of the foregoing description. Although the invention has been described with reference to specific exemplary embodiments, it will be evident that various modifications and changes may be made to these embodiments without departing from the broader spirit and scope of the invention. Accordingly, the specification and drawings are to be regarded in an illustrative sense rather than a restrictive sense.

What is claimed is:

1. A method for generating a document relating to a patient's medical diagnosis, comprising:
    employing a processor to execute computer executable instructions stored on a computer readable storage medium to implement the following acts:
        establishing one or more diagnostic codes, wherein each diagnostic code identifies a medical condition;
        storing one or more concepts associated with each diagnostic code, wherein each concept represents a different definition for the medical condition identified by the corresponding diagnostic code;
        storing one or more contexts associated with each diagnostic code, wherein each context represents corresponding contextual information for the medical condition identified by the corresponding diagnostic code;
        generating a set of queries for each of the one or more diagnostic codes using at least one of a subset of the one or more stored concepts or a subset of the one or more stored contexts as search criteria;
        submitting the set of queries to one or more databases;
        retrieving a list of links to content in the one or more databases that satisfy the search criteria, the retrieved list of links stored in a memory component;
        associating each link in the list with the diagnostic code and context used in the query that retrieved the respective link;
        receiving information about a patient, the information about the patient including diagnosis information based on a diagnosis of the patient;
        matching the information about the patient to at least one matching diagnostic code and at least one context associated with the at least one matching diagnostic code;
        pre-selecting a subset of the links associated with the at least one matching diagnostic code and the at least one matching context, the subset of links automatically pre-selected from the retrieved list of links independent of a query provided by a user for the subset of links; and
        generating at least one new document, wherein the at least one new document comprises the pre-selected subset of links and at least a portion of the information received about the patient.

2. The method of claim 1 wherein the diagnosis information comprises at least one diagnosis code, wherein each diagnosis code indicates a condition of the patient based on the diagnosis.

3. The method of claim 2 wherein the at least one diagnosis code comprises codes according to the International Classification of Disease (ICD).

4. The method of claim 3 wherein the diagnosis information comprises at least one description describing the condition of the patient based on the diagnosis.

5. The method of claim 1 wherein the information about the patient further comprises information selected from the group consisting of the patient's personal information, prescription information, laboratory information, procedures information, materials and supplies information and injection information.

6. The method of claim 1 wherein each link comprises an address corresponding to a location of data relevant to the diagnostic code and context used in the query that retrieved the link.

7. The method of claim 6 wherein the address comprises a Uniform Resource Locator (URL).

8. The method of claim 1 wherein generating the set of queries comprises:
    constructing a set of queries based on the information received.

9. The method of claim 8 wherein constructing comprises:
    determining at least one diagnosis identifier from the information received.

10. The method of claim 9 wherein the at least one diagnosis identifier corresponds to a diagnosis code, and wherein the links associated with the corresponding diagnosis code are selected for inclusion in the subset of links.

11. The method of claim 9 wherein the at least one diagnosis identifier corresponds to a diagnosis description.

12. The method of claim 11 wherein the diagnosis description describes an agent that is causally related to the diagnosis information.

13. The method of claim 9 wherein the at least one diagnosis identifier is included in the diagnosis information received.

14. The method of claim 9 wherein the at least one diagnosis identifier is derived from the diagnosis information received.

15. The method of claim 9 further comprising:
    determining additional diagnosis identifiers that are equivalent to the one or more diagnosis identifiers;
    matching the additional diagnosis identifiers with one of the concepts;
    selecting the links associated with the diagnostic code for the matching concept for inclusion in the subset of links.

16. The method of claim 1 further comprising:
    allowing the patient to access the at least one document via a computer network.

17. The method of claim 16 further comprising:
    allowing the patient to provide feedback or comments with respect to the information comprised in the at least one document.

18. The method of claim 17 wherein the computer network is selected from the group consisting of a local area network, a wide area network, and the Internet.

19. The method of claim 1 wherein the contextual information includes at least one of a weight, an age and a sex.

20. The method of claim 1 wherein the at least one new document includes a list of data sources associated with a parent diagnosis code when a list of data sources associated with a child diagnosis code cannot be identified, wherein the parent diagnosis code is included in a first classification in a hierarchy of diagnosis code classifications that includes a second classification that includes the diagnosis code.

21. A computer-readable storage medium comprising instructions that, when executed by a computer, cause the computer to perform operations comprising:

storing a set of diagnostic codes representing medical conditions, each diagnostic code having an associated code definition, one or more conceptual equivalencies, and one or more contexts relevant to the medical condition;

generating and storing at least one query for each stored diagnostic code utilizing as search criteria at least one of the one or more stored conceptual equivalencies or the at least one or more stored contexts;

retrieving and storing a list of data source links from one or more external data sources that satisfy the search criteria;

associating each retrieved data source link with the at least one or more stored contexts and the stored diagnostic code used to generate the query that retrieved the link;

receiving information about a patient, the information about the patient including diagnosis information and at least one patient-specific context based on a diagnosis of the patient;

upon receiving the information about the patient, performing a query function to pre-select from a database a subset of the data source links associated with a stored diagnostic code and at least one or more stored contexts matching the received information about the patient, the subset of data source links automatically pre-selected from the stored list of data source links independent of a query provided by a user for the subset of data source links, the computer being operable to:

select a set of queries comprising search criteria based on the received information about the patient, the set of queries selected from the stored queries associated with at least one stored diagnostic code and at least one or more stored contexts that correspond to the received information about the patient;

automatically execute the selected set of queries to retrieve the subset of data source links; and generating at least one new document comprising the subset of data source links pre-selected from the database.

22. The computer-readable storage medium of claim 21 wherein the diagnosis information comprises at least one diagnosis code, each diagnosis code indicating a condition of the patient based on the diagnosis.

23. The computer-readable storage medium of claim 21 wherein the diagnosis information comprises at least one description describing a medical condition of the patient based on the diagnosis.

24. A computer-readable storage medium comprising:

computer-readable instructions, the computer-readable instructions including instructions that when executed by at least one processor cause the at least one processor to perform the following acts:

establishing one or more diagnostic codes, wherein each diagnostic code identifies a medical condition;

storing one or more concepts associated with each diagnostic code, wherein each concept represents a different definition for the medical condition identified by the corresponding diagnostic code;

storing one or more contexts associated with each diagnostic code, wherein each context represents a corresponding contextual information for the medical condition identified by the corresponding diagnostic code;

generating a set of queries for each of the one or more diagnostic codes using at least one of a subset of the one or more stored concepts or a subset of the one or more stored contexts as search criteria;

submitting the set of queries to one or more databases;

retrieving a list of links to content in the one or more databases that satisfy the search criteria, the retrieved list of links stored in a memory component;

associating each link in the list with the diagnostic code and context used in the query that retrieved the respective link;

receiving information about a patient, wherein the information about the patient comprises diagnosis information based on a diagnosis of the patient;

matching the information about the patient to at least one matching diagnostic code and at least one context associated with the at least one matching diagnostic code;

pre-selecting a subset of the links associated with the at least one matching diagnostic code and the at least one matching context, the subset of links automatically pre-selected from the retrieved list of links independent of a query provided by a user for the subset of links; and generating at least one new document, wherein the at least one new document comprises the pre-selected subset of links and at least a portion of the information received about the patient.

\* \* \* \* \*